(12) United States Patent
Nelson

(10) Patent No.: US 9,999,561 B2
(45) Date of Patent: Jun. 19, 2018

(54) SHOULDER AND/OR KNEE PHYSICAL THERAPY AND RANGE OF MOTION DEVICE

(71) Applicant: Carol Nelson, Owatonna, MN (US)

(72) Inventor: Carol Nelson, Owatonna, MN (US)

( * ) Notice: Subject to any disclaimer, the term of this patent is extended or adjusted under 35 U.S.C. 154(b) by 0 days. days.

(21) Appl. No.: 15/840,423

(22) Filed: Dec. 13, 2017

(65) Prior Publication Data

US 2018/0098905 A1    Apr. 12, 2018

Related U.S. Application Data

(63) Continuation-in-part of application No. 14/952,554, filed on Nov. 25, 2015.

(60) Provisional application No. 62/085,217, filed on Nov. 26, 2014.

(51) Int. Cl.
A63B 23/00    (2006.01)
A61H 1/02    (2006.01)
A61B 5/11    (2006.01)

(52) U.S. Cl.
CPC ............... *A61H 1/024* (2013.01); *A61B 5/11* (2013.01); *A61H 1/0281* (2013.01); *A61H 2201/0123* (2013.01); *A61H 2201/0126* (2013.01); *A61H 2201/0192* (2013.01); *A61H 2201/1253* (2013.01); *A61H 2201/164* (2013.01); *A61H 2201/1635* (2013.01); *A61H 2201/1676* (2013.01); *A61H 2203/0431* (2013.01); *A61H 2205/062* (2013.01); *A61H 2205/104* (2013.01)

(58) Field of Classification Search
CPC .................. A61H 1/024; A61H 1/0281; A61H 2201/1635; A61H 2201/0123; A61H 2201/01253; A61H 2201/164; A61H 2201/0126; A61H 2201/1676; A61H 2201/0192; A61H 2203/0431; A61H 2205/104; A61H 2205/062; A63B 21/08; A63B 21/159; A63B 23/1245; A63B 23/1254; A63B 23/1263; A63B 23/1272
See application file for complete search history.

(56) References Cited

U.S. PATENT DOCUMENTS

| 2,921,791 | A | * | 1/1960 | Berne | ............... A63B 21/015 248/188.1 |
| 3,013,799 | A | * | 12/1961 | Wise | ............... A63B 21/015 482/118 |
| 3,475,024 | A | * | 10/1969 | Neil | ............... A63B 21/0615 482/97 |
| 3,588,101 | A | * | 6/1971 | Jungreis | ............. A63B 21/0023 177/24 |

(Continued)

*Primary Examiner* — Joshua Lee
(74) *Attorney, Agent, or Firm* — Vidas Arrett & Steinkraus

(57) ABSTRACT

A physical therapy device comprising a bench, having a seating surface and legs and a pair of horizontal supports positioned to either side of the knees of a person seated on the bench, a quick release securing device connected to each of the pair of supports, a rail connected to one of the quick release securing devices, a body pivotally attached to said rail, a foot rest attached to said rail and the foot rest and rail arranged to rotate with respect to said body about a pivot axis, the body having an adjustment mechanism to adjust the amount of force required to rotate the rail with respect to the body, wherein said body is repositionable between first and second positions, to provide physical therapy to the knee.

4 Claims, 35 Drawing Sheets

(56) References Cited

U.S. PATENT DOCUMENTS

| | | | | |
|---|---|---|---|---|
| 3,614,108 A * | 10/1971 | Garten | A63B 69/365 | 473/229 |
| 4,323,236 A * | 4/1982 | Szabo | A63B 21/0615 | 482/97 |
| 4,773,398 A * | 9/1988 | Tatom | A61H 1/0274 | 482/139 |
| 5,013,034 A * | 5/1991 | March | A63B 21/015 | 482/115 |
| 5,080,350 A * | 1/1992 | Schofield | A63B 23/12 | 482/131 |
| 5,179,939 A * | 1/1993 | Donovan | A61H 1/0281 | 482/4 |
| 5,186,695 A * | 2/1993 | Mangseth | A63B 21/0058 | 434/247 |
| 5,558,624 A * | 9/1996 | Hepburn | A63B 21/015 | 482/130 |
| 6,007,500 A * | 12/1999 | Quintinskie, Jr. | A61H 1/0281 | 601/33 |
| 7,837,599 B2 * | 11/2010 | Kowalczewski | G06F 19/3481 | 482/44 |
| 8,974,354 B1 * | 3/2015 | Nelson | A63B 21/08 | 482/94 |
| 9,713,738 B2 * | 7/2017 | Schrag | A63B 21/0087 | |
| 9,744,092 B2 * | 8/2017 | Fu | A61H 1/0281 | |
| 2004/0147376 A1 * | 7/2004 | Gautier | A63B 23/1245 | 482/93 |
| 2004/0157711 A1 * | 8/2004 | Regev | A63B 21/06 | 482/142 |
| 2005/0176558 A1 * | 8/2005 | Huang | A63B 21/06 | 482/93 |
| 2006/0040799 A1 * | 2/2006 | Pompile | A63B 21/0552 | 482/92 |
| 2006/0041205 A1 * | 2/2006 | Ladd, Jr. | A61H 1/0281 | 601/5 |
| 2006/0166797 A1 * | 7/2006 | Hamer | A63B 21/055 | 482/121 |
| 2007/0184941 A1 * | 8/2007 | Krietzman | A63B 21/0615 | 482/93 |
| 2007/0282228 A1 * | 12/2007 | Einav | A61B 34/30 | 601/33 |
| 2011/0287851 A1 * | 11/2011 | Okesaku | A63B 21/0615 | 473/229 |
| 2012/0035512 A1 * | 2/2012 | Su | A61H 1/0281 | 601/5 |
| 2015/0297942 A1 * | 10/2015 | Tully | A63B 21/16 | 482/94 |

* cited by examiner

FIG. 12

SHOULDER AND/OR KNEE PHYSICAL THERAPY AND RANGE OF MOTION DEVICE

CROSS-REFERENCE TO RELATED APPLICATIONS

This application is a continuation-in-part of U.S. patent application Ser. No. 14/952,554, filed Nov. 25, 2015, which in turns claims priority to U.S. Provisional patent application No. 62/085,217 filed Nov. 26, 2014, the entire contents of both of which are hereby incorporated by reference.

BACKGROUND OF THE INVENTION

This invention relates to physical therapy devices, medical devices and exercise devices.

Many people suffer from pain and/or loss of range of motion in joints, such as the shoulder and elbow. Causes for pain and/or loss of range of motion can be anything from physical injury to old age.

A treatment for injury can often include physical therapy and exercise. Due to the complex movements of the shoulder, several different exercises may be used to flex the shoulder in different ways. When machines are used to assist in exercising, generally a unique machine is provided for each particular exercise.

There remains a need for a device capable of exercising the shoulder in multiple ways. There remains a need for a device capable of exercising the shoulder as well as the elbow.

During physical therapy, a range of motion of a joint may be measured on an ongoing basis. A physical therapist may use one device to measure a range of motion and a separate device for exercising the joint.

There remains a need for a device capable of exercising a joint as well as performing a range of motion analysis.

The invention is not limited to medical settings. Any person who desires to maximize their mobility, functional ability and quality of life can benefit from exercising the shoulder. When using external resistance, such as a machine that provides weights or flexing bands, the resistance provided is generally considered one-way, wherein the biasing provided operates in a single direction.

There remains a need for an exercise device that provides two-way resistance.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

These and other embodiments which characterize the invention are pointed out with particularity in the claims annexed hereto and forming a part hereof. However, for a better understanding of the invention, its advantages and objectives obtained by its use, reference can be made to the drawings which form a further part hereof and the accompanying descriptive matter, in which there are illustrated and described various embodiments of the invention.

BRIEF DESCRIPTION OF THE DRAWINGS

A detailed description of the invention is hereafter described with specific reference being made to the drawings.

FIG. 8-1 shows the counterweight adapter in more detail.

FIG. 12 shows the hook of FIG. 11 in more detail.

DETAILED DESCRIPTION OF THE INVENTION

Figure 1:
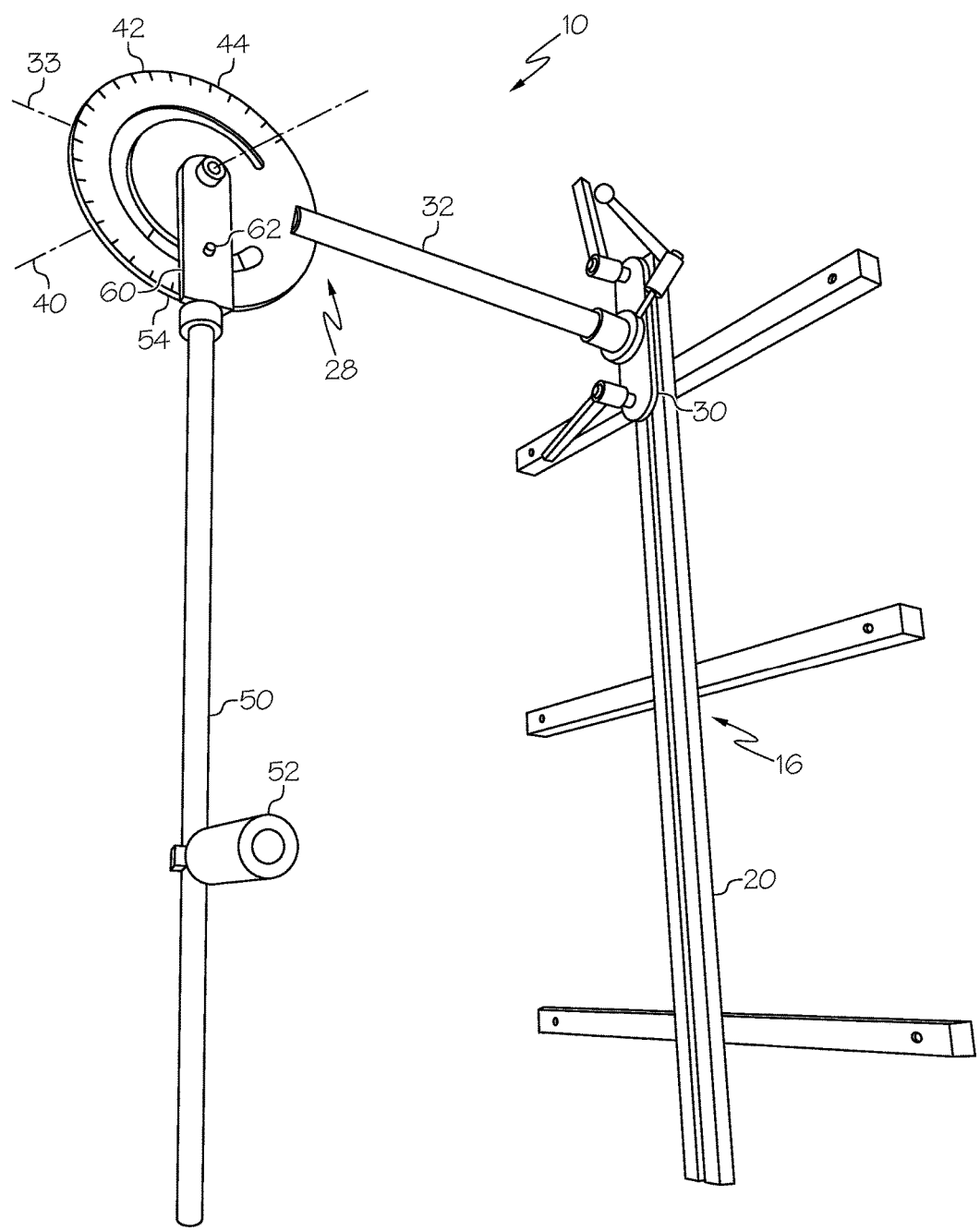
FIG. 1 shows an embodiment of a physical therapy device.

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

FIG. 1 shows an embodiment of the device 10. In some embodiments, the device 10 comprises a frame 16, a body 28 supported by the frame 16 and an arm 50 that is pivotable with respect to the body 28.

The frame 16 can have any suitable shape or configuration. Desirably, the frame 16 is supported by any suitable supporting surface, such as a floor, wall, ceiling, etc. In some embodiments, the frame 16 is attached to the supporting surface, for example using fasteners. The embodiment shown in FIG. 1 is configured for mounting to a wall.

In some embodiments, the body 28 is repositionable with respect to the frame 16, for example being attachable to the frame 16 in a plurality of locations. This allows for adjustment of a location of the body 28, for example allowing the device 10 to be adjusted based upon a user's height.

In some embodiments, the frame 16 comprises a rail 20, and the body 28 can be repositioned along a length of the rail 20. In some embodiments, the rail 20 is continuous from a first end to a second end, and the body 28 can be positioned at any location along the length of the rail 20. When the rail 20 extends vertically, repositioning the body 28 can adjust a height of the body 28 with respect to a floor or a user.

In some embodiments, the device 10 comprises a mount 30 that attaches between the body 28 and the frame 16. For example, the mount 30 is attachable to the frame 16, and the body 28 is attachable to the mount 30. In some embodiments, the mount 30 is attachable to the frame 16 in a plurality of positions. In some embodiment, the body 28 is attachable to the mount 30 in a plurality of orientations.

In some embodiments, the body 28 comprises a stem 32 and a plate 42. In some embodiments, the stem 32 is arranged for attachment to the mount 30, or directly to the frame 16. In some embodiments, the arm 50 is attached to the plate 42.

Desirably, the arm 50 is arranged to pivot with respect to the body 28. For example, the arm 50 can be arranged to pivot about a pivot axis 40. In some embodiments, the pivot axis 40 is oriented orthogonal to a planar surface of the plate 42.

The arm 50 may be arranged to pivot about any suitable angle or arc length. In some embodiments, the arm 50 can pivot at least 180 degrees. In some embodiments, the arm 50 can pivot at least 270 degrees.

Desirably, the arm 50 comprises a grip 52. The grip 52 can be grasped by a user, and the arm 50 can be rotated by the user about the pivot axis 40. For example, a user can pivot the arm 50 about the pivot axis 40, thereby moving a portion of the user's body while being guided by the device 10. This can provide physical therapy to a portion of the user's body, such as a shoulder.

In some embodiments, the grip 52 is repositionable with respect to the arm 50. In some embodiments, the grip 50 can be moved along a length of the arm 50. In some embodiments, an orientation of the grip 50 can be adjusted with respect to the pivot axis 40, for example an axis of the grip 50 can be oriented parallel to the pivot axis 40 in a first position, and oriented at an angle to the pivot axis 40 in a second position.

Figure 2:
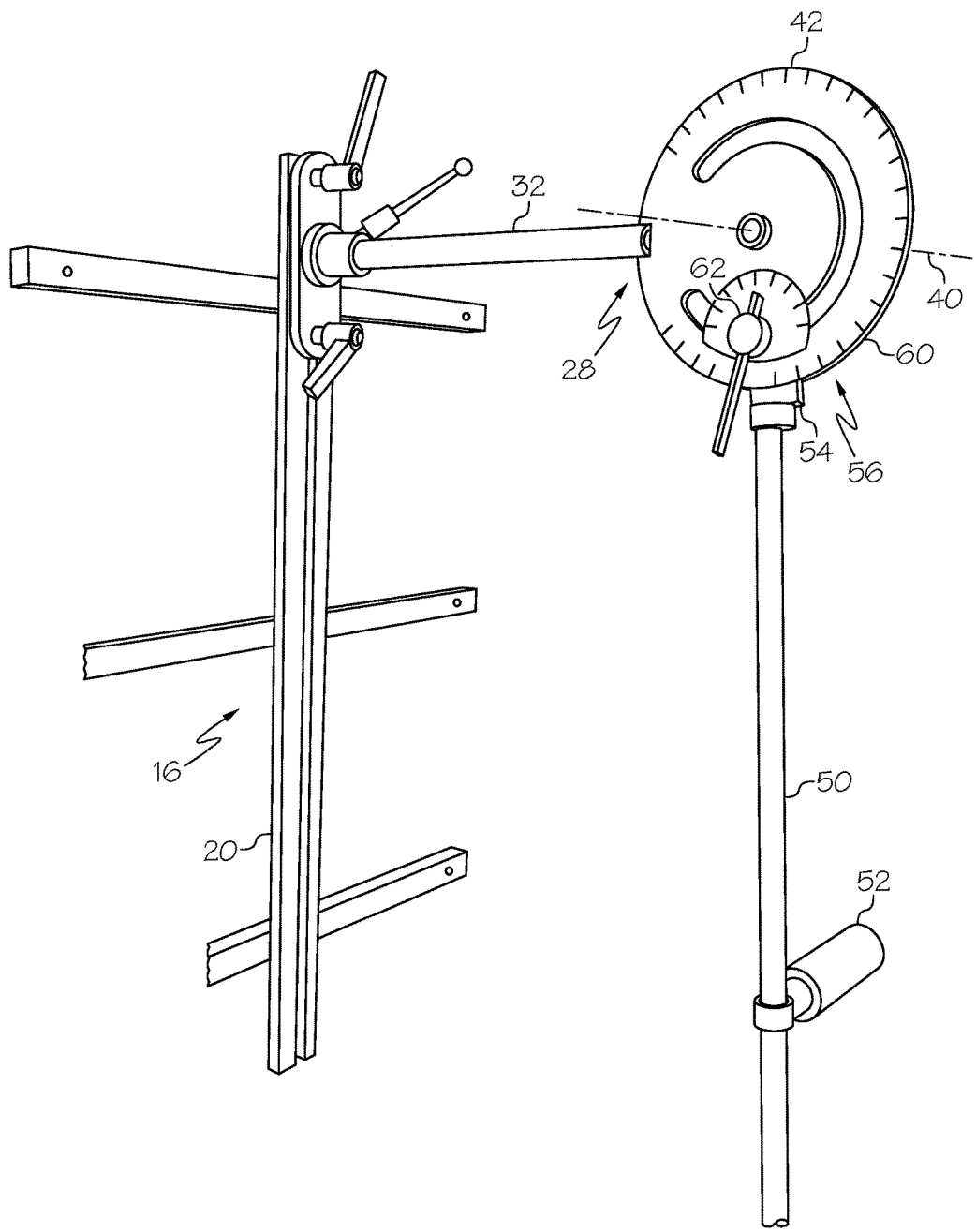
FIG. 2 shows the device of FIG. 1 from another angle.

FIG. 2 shows the device 10 of FIG. 1 from a different angle, wherein an opposite face of the plate 42 is visible.

In some embodiments, the device 10 comprises an adjustment mechanism 56 arranged to adjust an amount of force required to pivot the arm 50 with respect to the body 28. Any suitable adjustment mechanism 56 can be used. In some embodiments, one or more friction pads 60 are arranged to move with the arm 50 and contact the plate 42. In some embodiments, a fastener 62 is used to clamp the friction pad(s) 60 against the plate 42. Adjustment of the fastener 62 will adjust the clamping force applied, thus adjusting the normal force of the friction pad(s) 60 against the plate 42 and the force required to move the arm 50 with respect to the plate 42.

In some embodiments, a friction pad 60 comprises a composite, for example UHMW Polyethylene.

In some embodiments, one or more face surfaces of the plate 42 comprises a scale 44. For example, in some embodiments, a scale 44 comprises a rotational scale labeled with degrees. In some embodiments, the arm 50 comprises a pointer 54 that can be used in conjunction with the scale 44. In some embodiments, the arm 50 has a first position, for example as shown in FIG. 1. In some embodiments, the arm 50 is oriented vertically in the first position. In some embodiments, the pointer 54 points to a reading of zero on the scale 44 when the arm 50 is in the first position. A user can move the arm 50 about the pivot axis 40, for example working the shoulder. The scale 44 can be used to measure a range of motion of which the user is capable.

In some embodiments, an opposite face of the plate 42 comprises a second scale arranged differently from the first scale. For example, the second scale may have a zero point when the arm 50 is oriented horizontally, and may increase in angle when the arm 50 is rotated in either direction.

Figure 3:
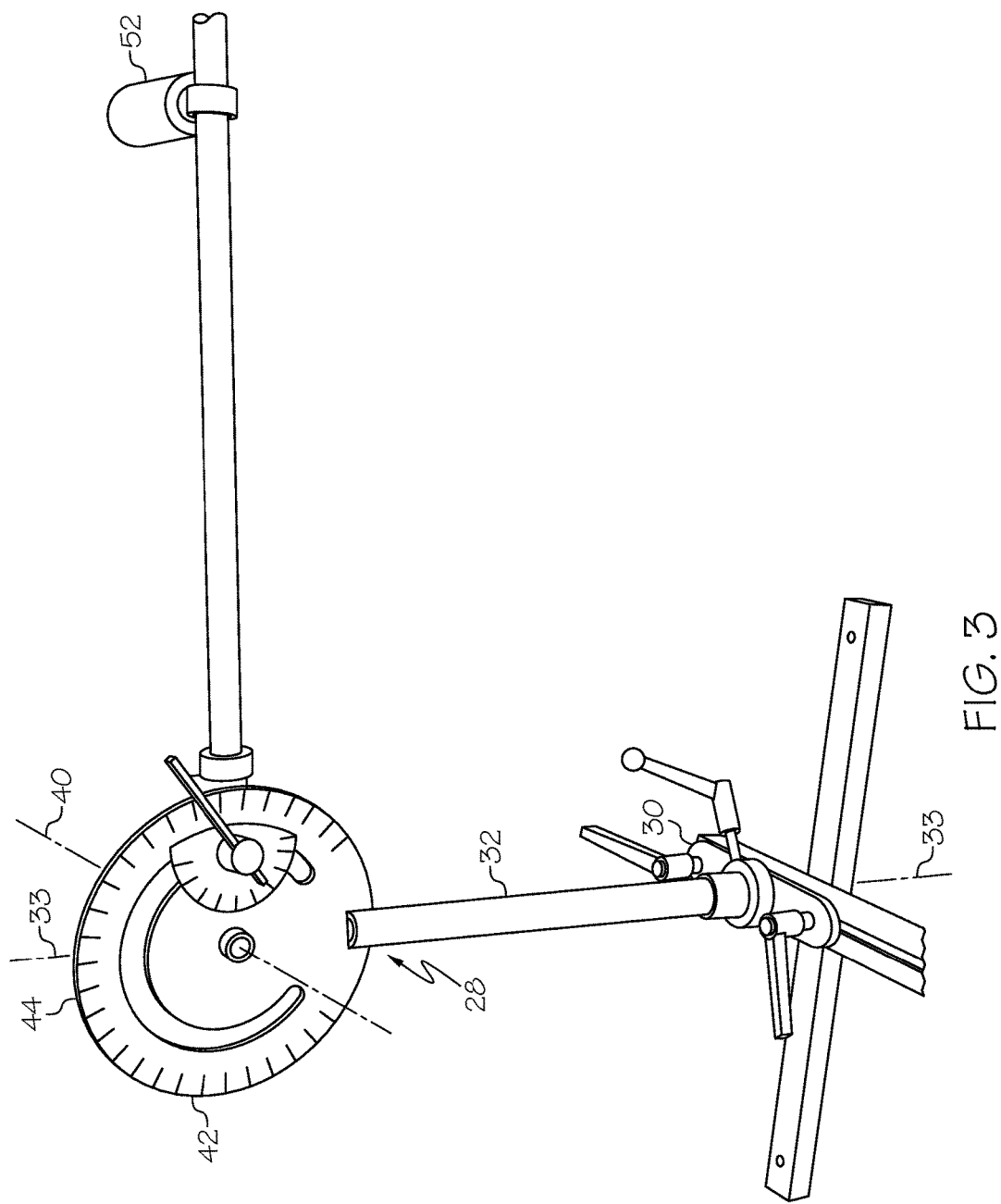
FIG. 3 shows the device of FIG. 1 in another orientation.

FIG. 3 shows the device 10 of FIG. 1 in another orientation. Desirably, the body 28 is repositionable with respect to the frame 16 and capable of being attached to the frame 16 in a plurality of positions. In some embodiments, the pivot axis 40 is repositioned when the body 28 is repositioned with respect to the frame 16. In some embodiments, the body 28 is repositionable with respect to the frame 16. In some embodiments, the body 28 is repositionable about an axis 33 oriented orthogonal to the pivot axis 40. In some embodiments, the body 28 is rotatable about a longitudinal axis of the stem 32. As shown in FIG. 3, the stem 32 is received in the mount 30 and can be positioned in any rotational orientation.

In the configuration shown in FIG. 3, the pivot axis 40 extends vertically, and the arm 50 moves in a horizontal plane.

Figure 4:
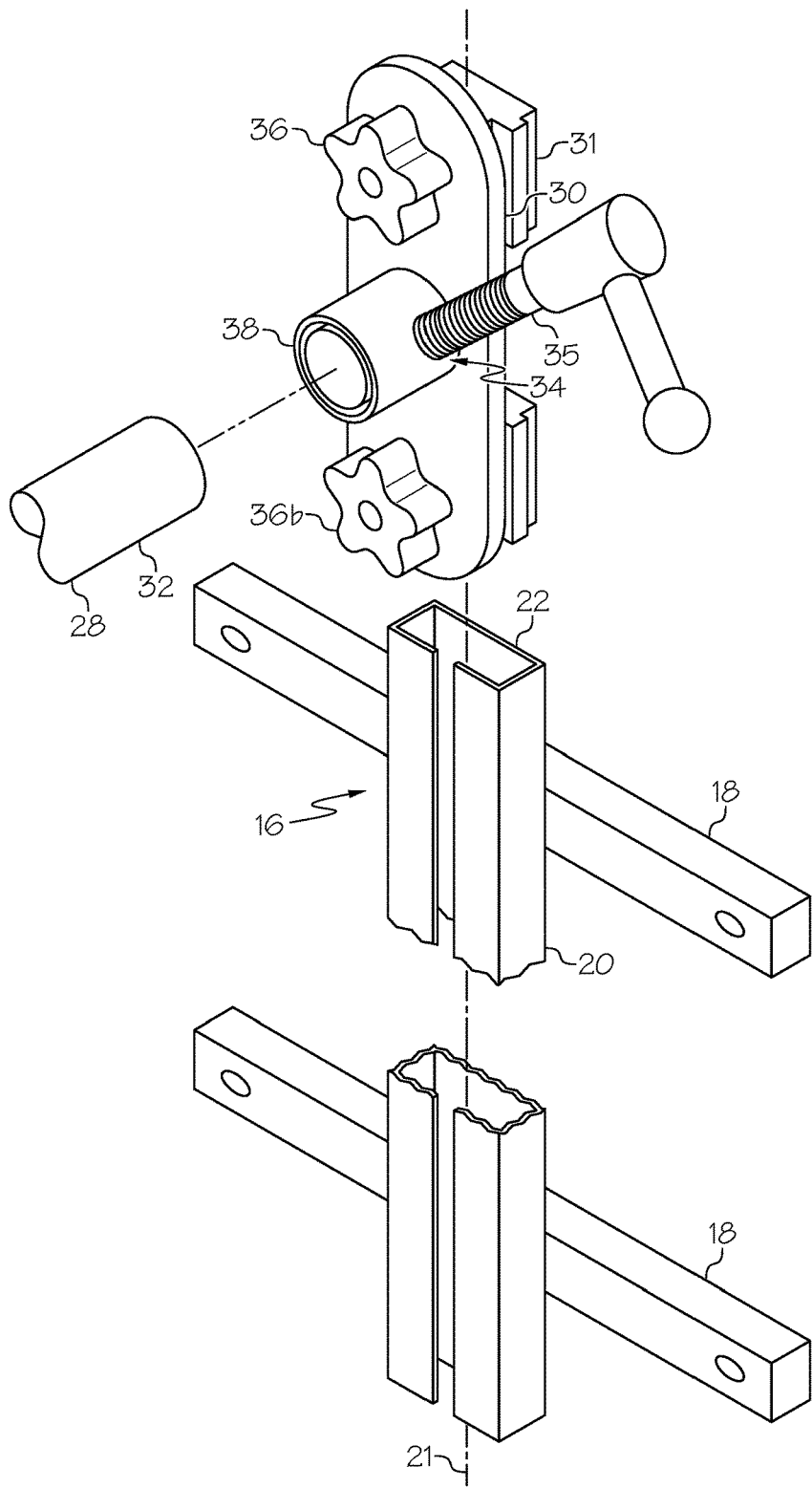
FIG. 4 shows an embodiment of a frame of the device.

FIG. 4 shows an embodiment of a frame 16 and an embodiment of a mount 30 in greater detail.

In some embodiments, a frame 16 comprises a rail 20 that defines a longitudinal axis 21. In some embodiments, the rail 20 is attached directly to a supporting surface. In some embodiments, the frame 16 comprises one or more cross-members 18 for added stability.

In some embodiments, the rail 20 is straight and continuous along its length. In some embodiments, the rail 20 comprises a channel 22, such as a T-slot. In some embodiments, the rail 20 is formed by a process of extrusion. Desirably, the channel 22 comprises a cavity formed in the rail, wherein an opening to the cavity has a smaller dimension than a distance across the cavity. This allows an object having a suitable shape (e.g. T-shape) to be engaged by the channel 22. In some embodiments, the rail 20 has a constant cross-sectional shape.

In some embodiments, the channel 22 is continuous along the length of the rail 20. In some embodiments, the mount 30 can be repositioned and secured at any suitable location along the length of the rail 20. In some embodiments, the height of the body 28 can be adjusted by adjusting the position of the mount 20.

Desirably, the mount 30 comprises a fastener 36 and an anchor 38. In some embodiments, the fastener 36 is arranged to secure the mount 30 to the frame 16. In some embodiments, the fastener 36 comprises a bolt and/or nut. For example, in some embodiments, a head of a bolt can be retained in the channel 22. A stem of the bolt can pass through the mount 30, and a nut can secure the mount 30 to the bolt. In some embodiments, the nut can comprise a knob. Alternatively, in some embodiments, a knob can comprise a threaded stem that passes through the mount 30 and engages a nut that is arranged to be retained in the channel 22 (e.g. a square nut or any other suitable shape).

In some embodiments the mount 30 comprises a second fastener 36b. In some embodiments, two fasteners 36, 36b are positioned on opposite sides of the anchor 38.

In some embodiments, the mount 30 comprises one or more pads 31 arranged to contact the frame 16. In some embodiments, a pad comprises a low friction material.

In some embodiments, a pad 31 comprises a raised portion that is constructed and arranged to occupy the opening of the channel 22. Thus, the pad 31 can act as a guide that facilitates linear adjustment of the mount 30 along a length of the rail 20.

Desirably, the anchor 38 is arranged to receive and attach to the body 28. In some embodiments, the stem 32 of the body 28 is received in the anchor 38. In some embodiments, the anchor 38 comprises a sleeve that extends around an outer perimeter of the stem 32. In some embodiments, the anchor 38 comprises a threaded aperture 34 and a threaded rod 35 arranged to be received in the aperture 34. The stem 32 can be received in the anchor 38, and the threaded rod 35 tightened against the stem 32, thereby fixing the stem 32 with respect to the anchor 38. In some embodiments, the anchor 38 is capable of receiving the stem 32 at any rotational orientation, and facilitates rotation of the body 28 with respect to the frame 16—thereby allowing rotation of the pivot axis 40 with respect to the frame 16.

Figure 5:
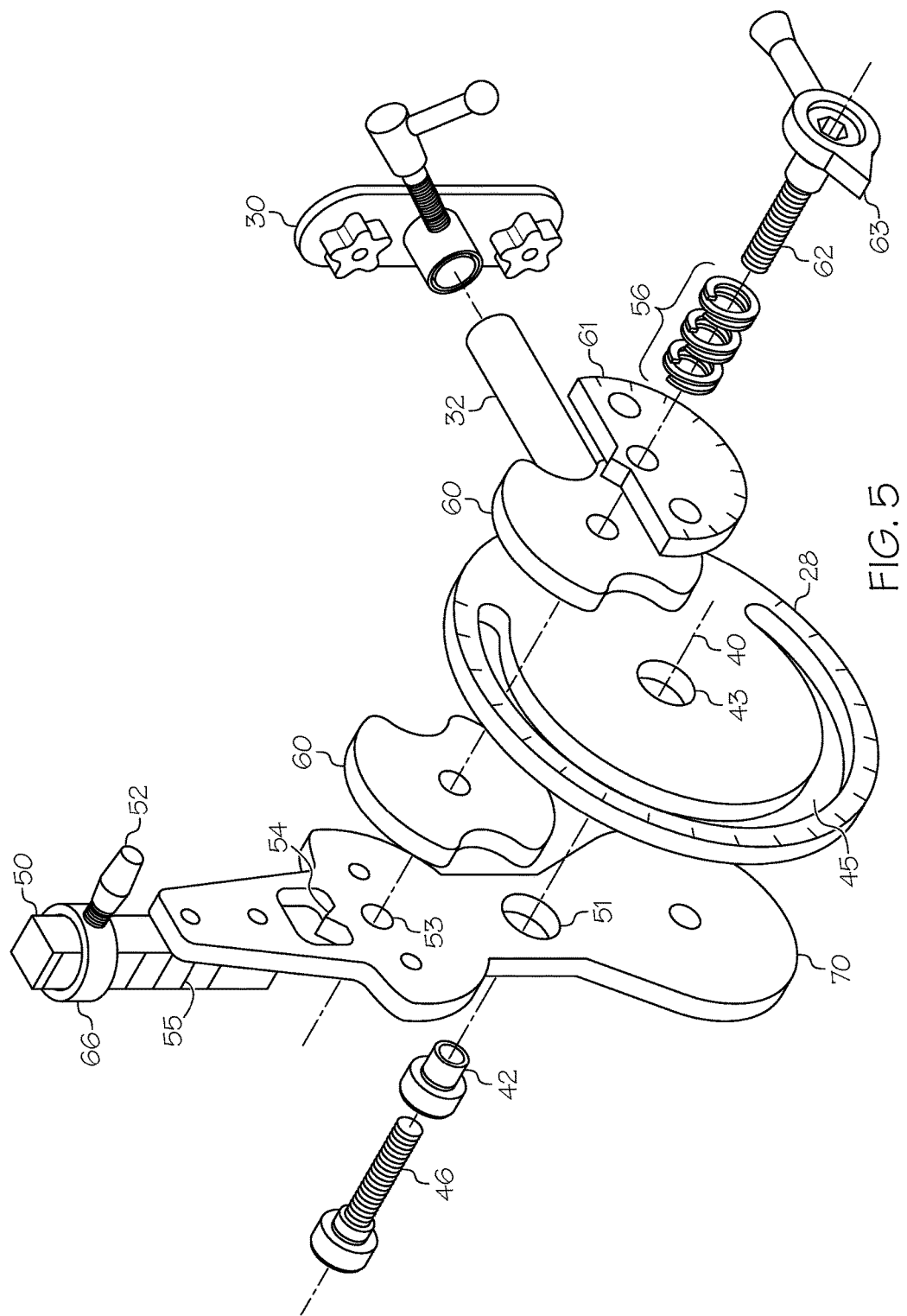
FIG. 5 shows an embodiment of a body and arm of the device.

FIG. 5 shows an embodiment of an anchor 30 and an embodiment of a body 28 and arm 50.

In some embodiments, the body 28 comprises a plate 42 that is circular in shape. In some embodiments, the plate 42 comprises an aperture 43 that receives a fastener 46 that attaches the arm 50 to the plate 42. In some embodiments, the aperture 43 is located centrally in the plate 42. In some embodiments, the arm 50 is arranged to pivot about the fastener 46, and the fastener 46 and/or aperture 43 are aligned on the pivot axis 40. In some embodiments, a sleeve 47 is positioned between the fastener 46 and the arm 50 and/or positioned between the fastener 46 and the plate 42. In some embodiments, the sleeve 47 is sized to allow tightening of the fastener 46 against the sleeve—thus, the arm 50 can be secured to the plate 42 with a connection that does not force the arm 50 against the plate 42 (e.g. low friction).

In some embodiments, the arm 50 comprises scale markings along its length. In some embodiments, the arm 50 comprises detents 55 that define attachment locations for the grip 52.

In some embodiments, the grip 52 comprises a ring 66 arranged to surround the arm 50. In some embodiments, the ring 66 comprises a threaded aperture arranged to receive a threaded stem of the grip 52. Thus, the threaded stem of the grip 52 can be tightened against the arm 50, securing the grip 52 in any suitable orientation. The grip 52 can be adjusted to any suitable position along the length of the arm 50, and the grip 52 can be oriented to extend from the arm 50 in any suitable direction.

Figure 6:
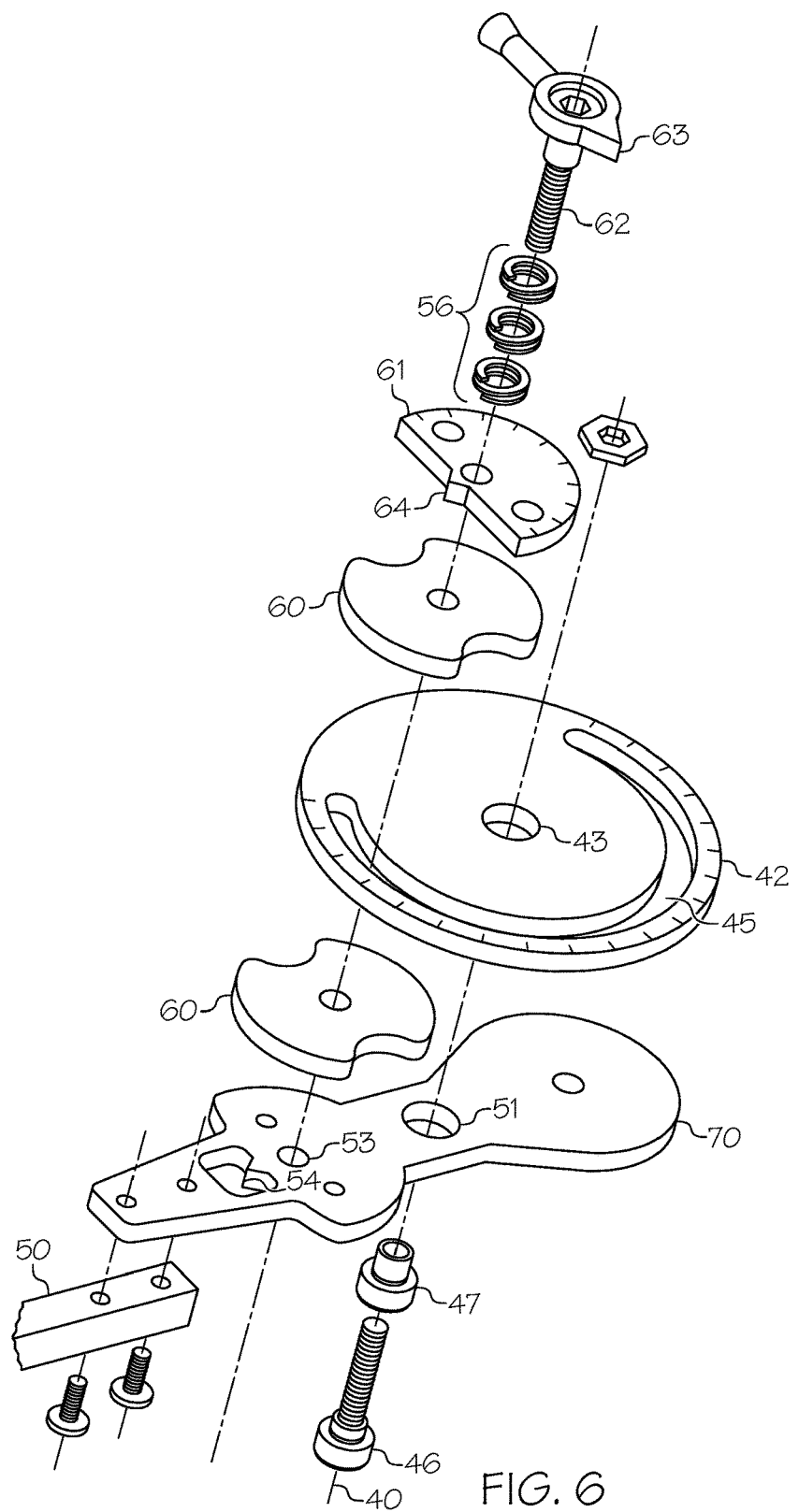
FIG. 6 shows an embodiment of a plate and an embodiment of an adjustment mechanism.

FIG. 6 shows an embodiment of a plate 42 and an embodiment of an adjustment mechanism 56.

With reference to FIGS. 5 and 6, in some embodiments, the arm 50 comprises a first aperture 51 arranged to receive the fastener 46 oriented upon the picot axis 40. In some embodiments, the arm 50 comprises a second aperture 53 that comprises a portion of the adjustment mechanism 56. In some embodiments, the second aperture 53 is threaded and arranged to receive a threaded portion of the fastener 62. In some embodiments, the plate 42 defines an arcuate opening 45, and the fastener 62 passes through the arcuate opening 45. In some embodiments, the arcuate opening 45 extends around the aperture 43 and is located a predetermined distance (e.g. radius) from the aperture 43.

In some embodiments, a first friction pad 60 and a second friction pad 60 are oriented on opposite sides of the plate 42. The fastener 62 can extend through the calibrated thrust washer 61 and first friction pad 60, the arcuate opening 45, the second friction pad 60 and engage the second aperture 53 in the arm 50. Tightening the fastener 62 will increase the clamping force of the spring washers 56, thereby adjusting an amount of friction or resistance to pivoting the arm 50 about the pivot axis 40.

In some embodiments, the fastener 62 includes a pointer 63 and the first friction pad 60 includes a scale. The pointer 63 can indicate a relative amount of resistance to pivoting the arm 50 provided by the adjustment mechanism 56.

In some embodiments, the first friction pad 60 comprises a pointer 64 arranged to indicate a rotational position of the arm 50, for example with respect to the plate 42. In some embodiments, pointer 64 is aligned on a longitudinal axis of the arm 50.

In some embodiments, the body 28 comprises an adjustment mechanism that allows reorientation of the axis 40 with respect to the frame 16. For example, in some embodiments, the body 28 comprises a hinge that can be arranged in multiple orientations. In some embodiments, a hinge is located on the stem 32. In a first hinge orientation, portions of the stem 32 located on opposite sides of the hinge are parallel. The pivot axis 40 can extend orthogonal to the stem 32. In a second hinge orientation, portions of the stem 32 located on opposite sides of the hinge are perpendicular to one another. In the second hinge orientation, the pivot axis 40 can extend parallel to a section of the stem 32, and the pivot axis 40 can be oriented orthogonally to its position in the first hinge orientation.

Figure 7:
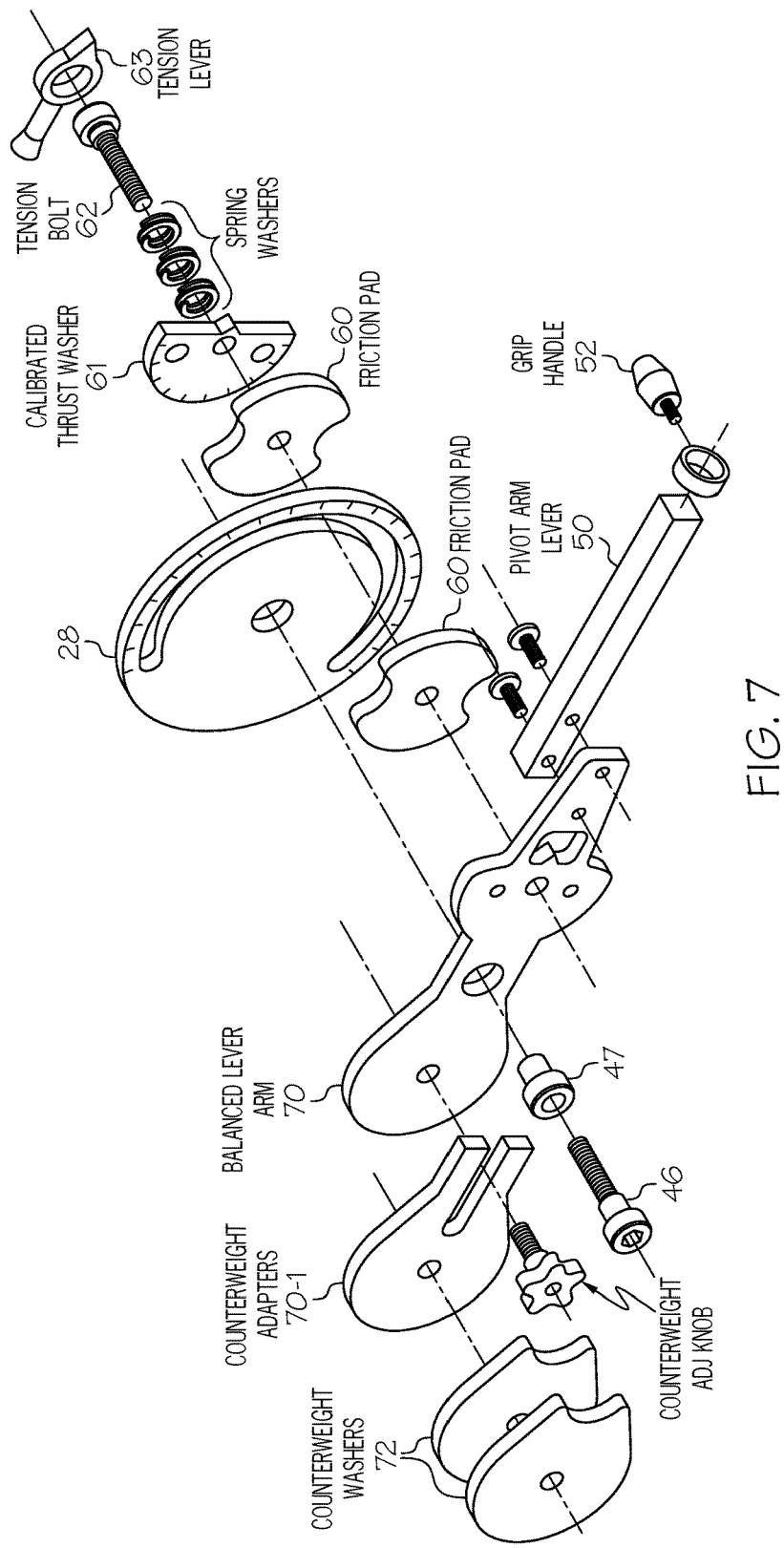
FIG. 7 shows an embodiment of a physical therapy device including a counterbalance.

FIG. 7 shows an embodiment including a balance lever arm 70, counterweight adapter 70-1, with an appropriate number of counterweight washers 72 to balance the pivot arm assembly when the grip handle 52 is position in any position on the pivot arm lever 50. This will allow the balanced pivot arm assembly, when left in any degree of rotation position and will remain balanced. This allows the amount of force required to activate the lever arm to remain constant through the entire range of rotation, in either the lift or downward rotations.

The reason the counterweight adapter 70-1 is required, is to balance the balanced lever arm assembly when the grip handle 52 is positioned any location on the pivot arm lever 50. This location will affect the center of the rotational gravity of the balanced lever arm assembly and will change accordingly affecting the rotational input force required. To counter balance the position of the mounting of the grip handle 52 on the pivot arm 50 will be accomplished by fix mounting the counterweight washers on the counterweight adapter allowing the counter weight adapter assembly to be adjusted by sliding the counterweight adapter on the balance lever arm 70, until the lever arm assembly is balanced.

Figure 8:
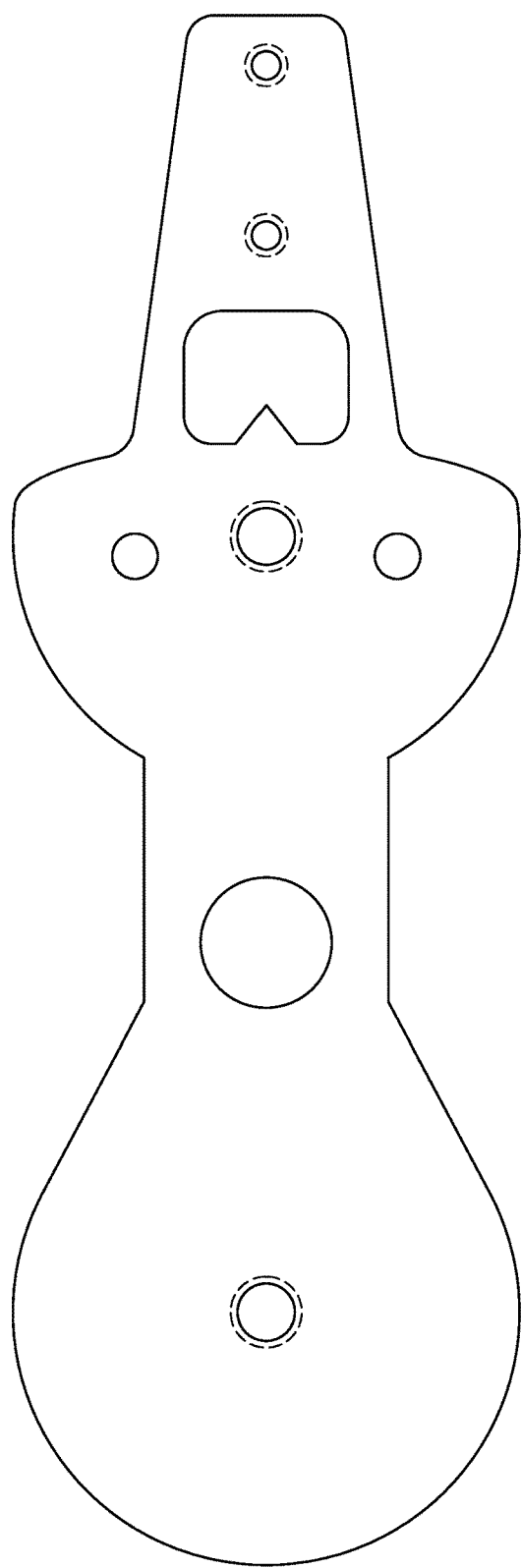
FIG. 8 shows the counterweight adapter of FIG. 7 in more detail.
Figures 1, 8:
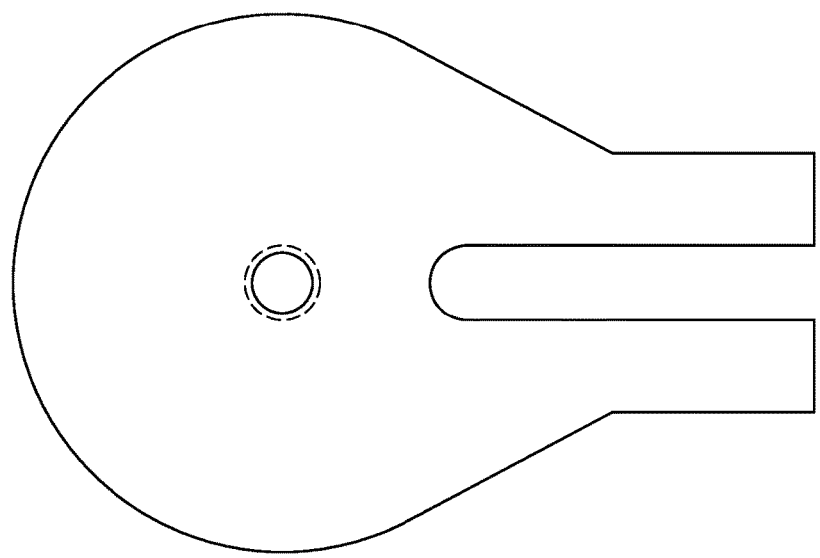

FIG. 8 shows the balance lever arm 70 in more detail.

FIG. 8-1 shows the counterweight adapter in more detail.

Figure 9:
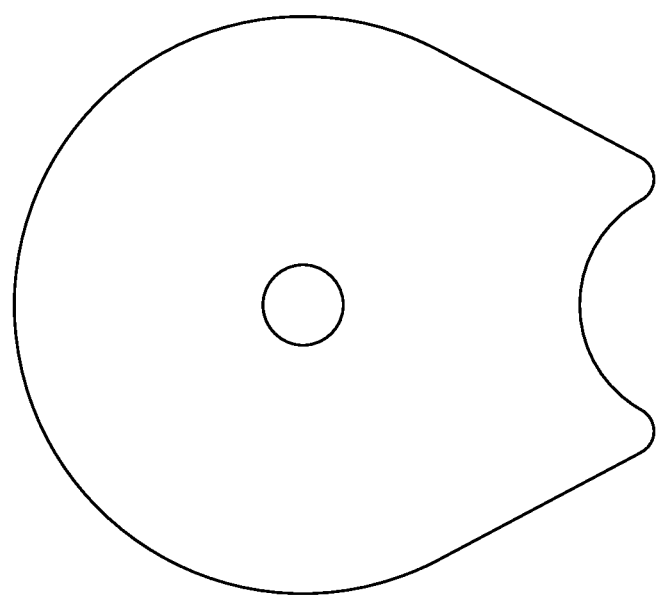
FIG. 9 shows the counterweight washer of FIG. 7 in more detail.

FIG. 9 shows a counterweight washer 72 in more detail.

Figure 10:
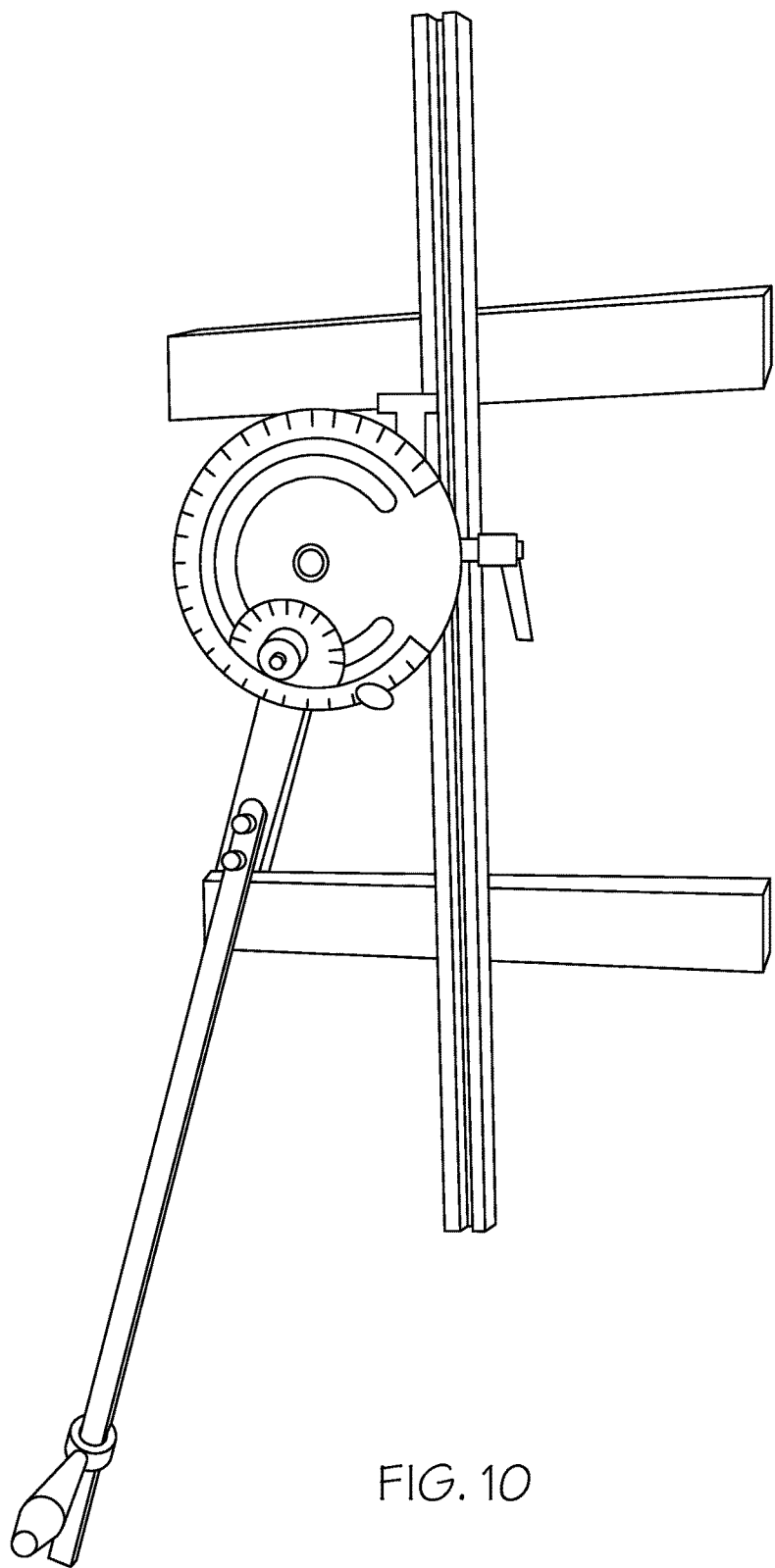
FIG. 10 shows the physical therapy device in a wall mount arrangement.

FIG. 10 shows the physical therapy device in a wall mount arrangement.

Figure 11:
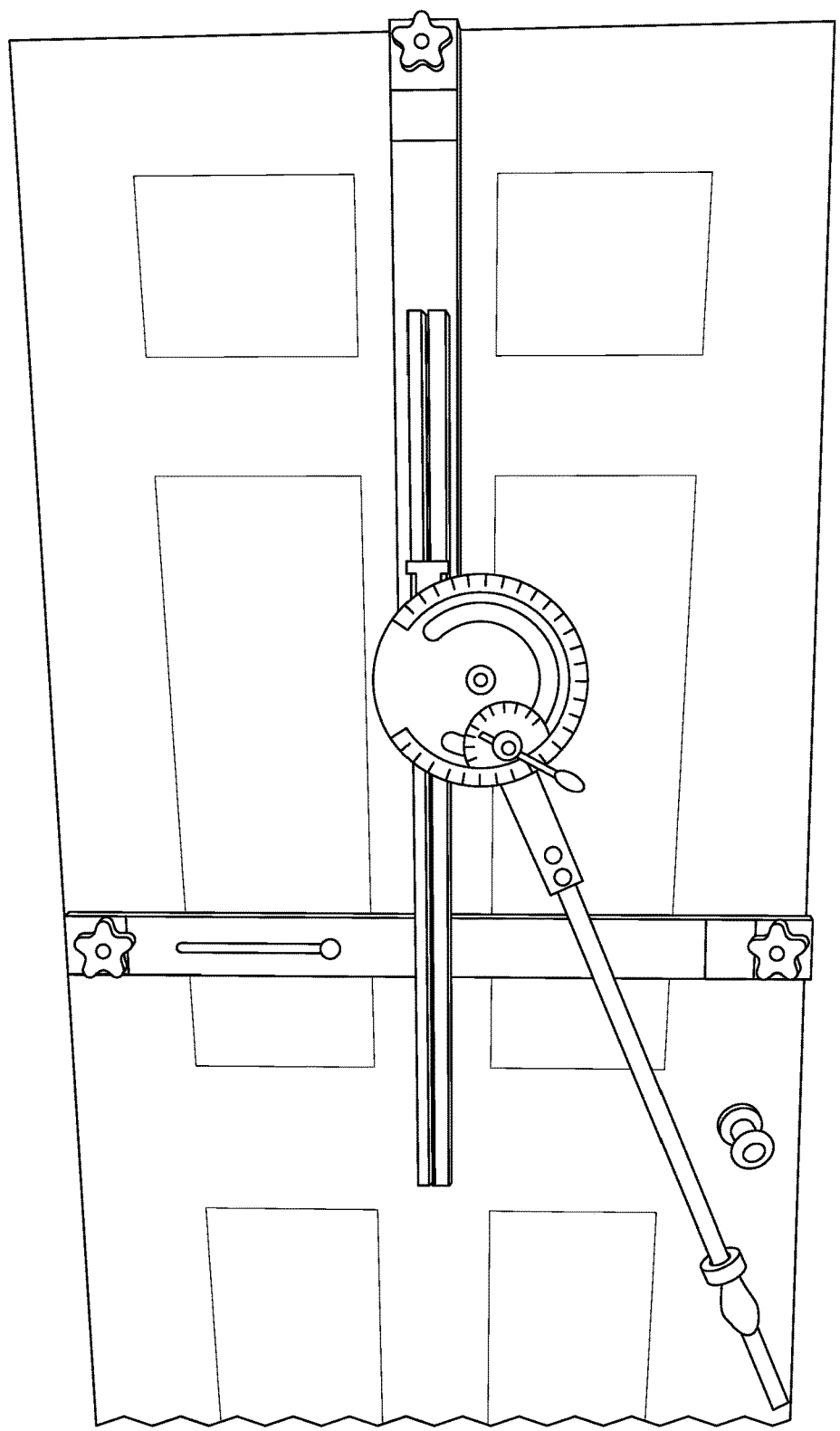
FIG. 11 shows the physical therapy device in a door mount arrangement.

FIG. 11 shows the physical therapy device in a door mount arrangement, with a hook arranged at the top to hang the device from the door and a door attachment portion to secure the device securely to the door.

Figure 12:
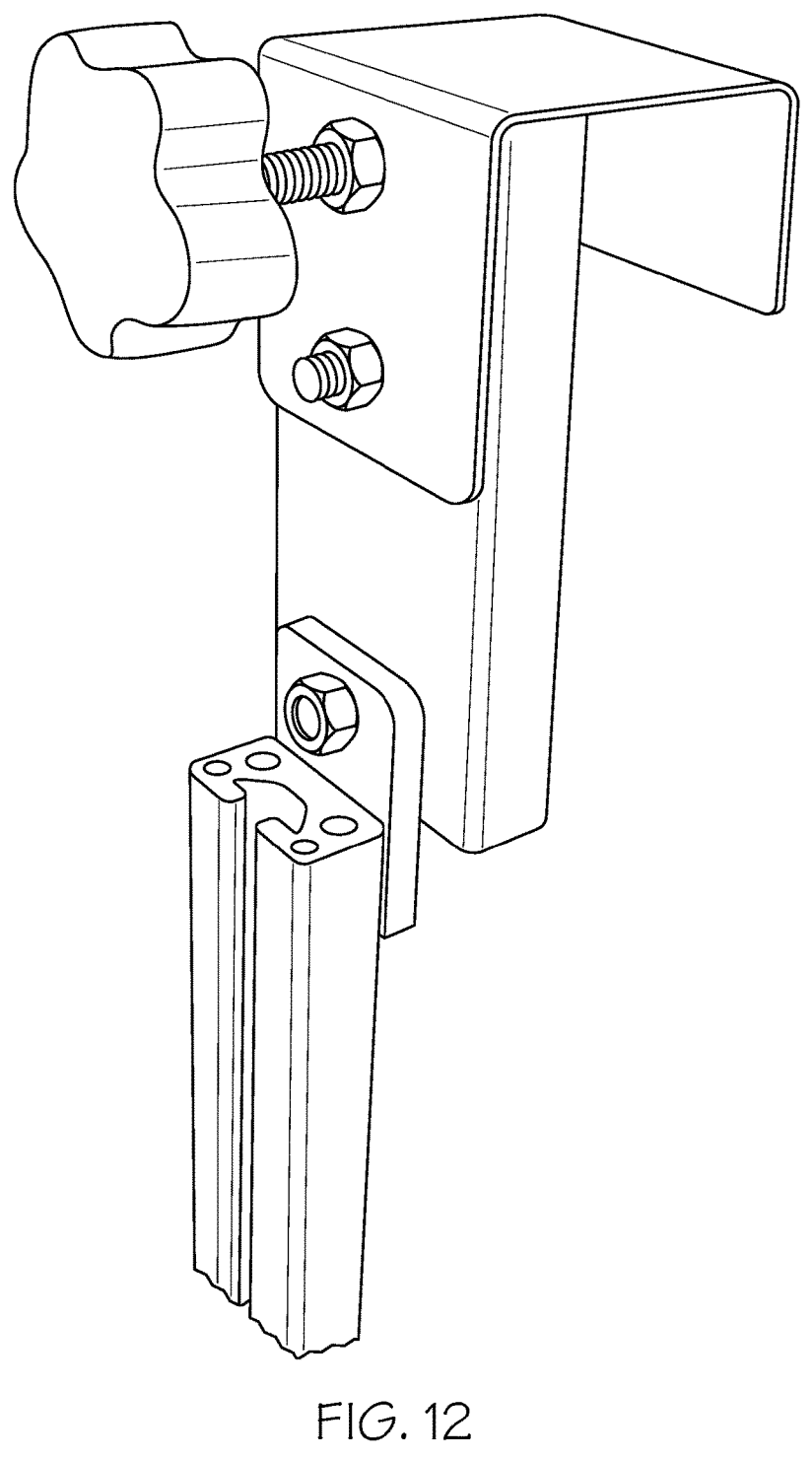

FIG. 12 shows the hook of FIG. 11 in more detail.

Figure 13:
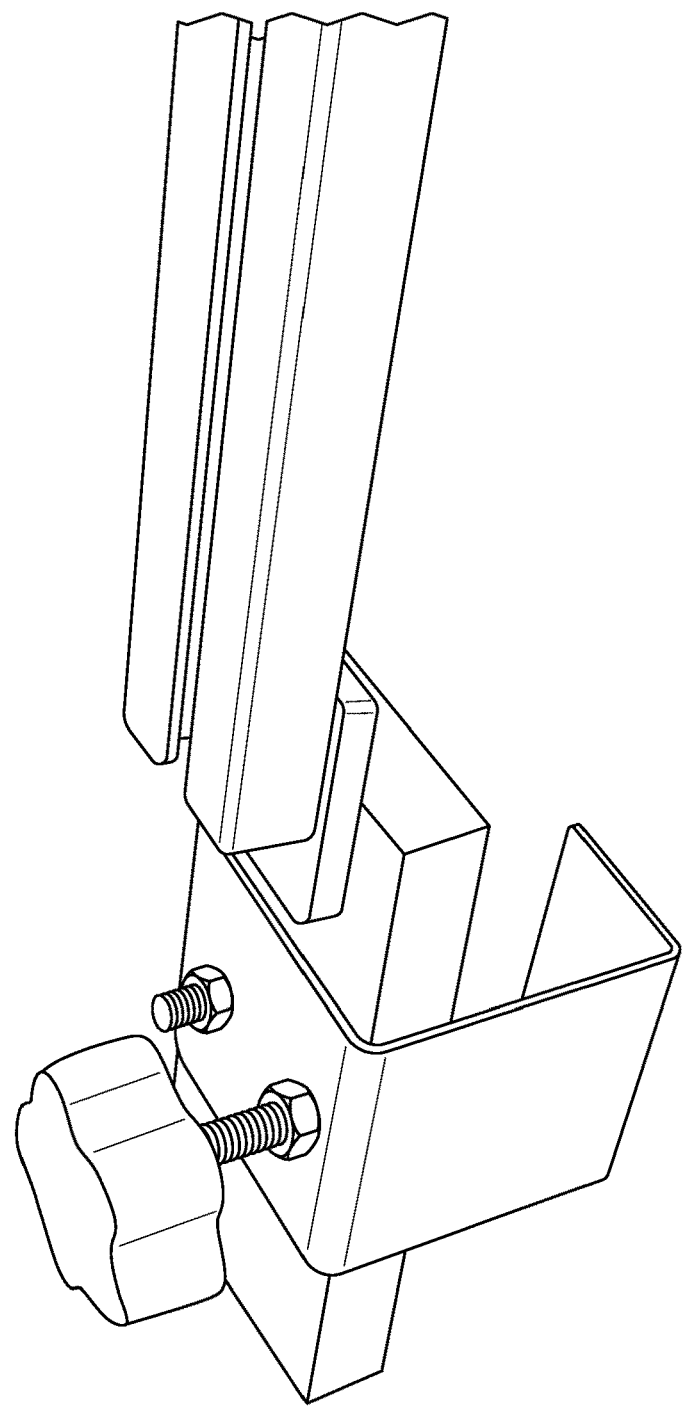
FIG. 13 shows the lower door mount attachment portion of FIG. 11 in more detail.

FIG. 13 shows the lower door mount attachment portion of FIG. 11 in more detail.

Figure 14:
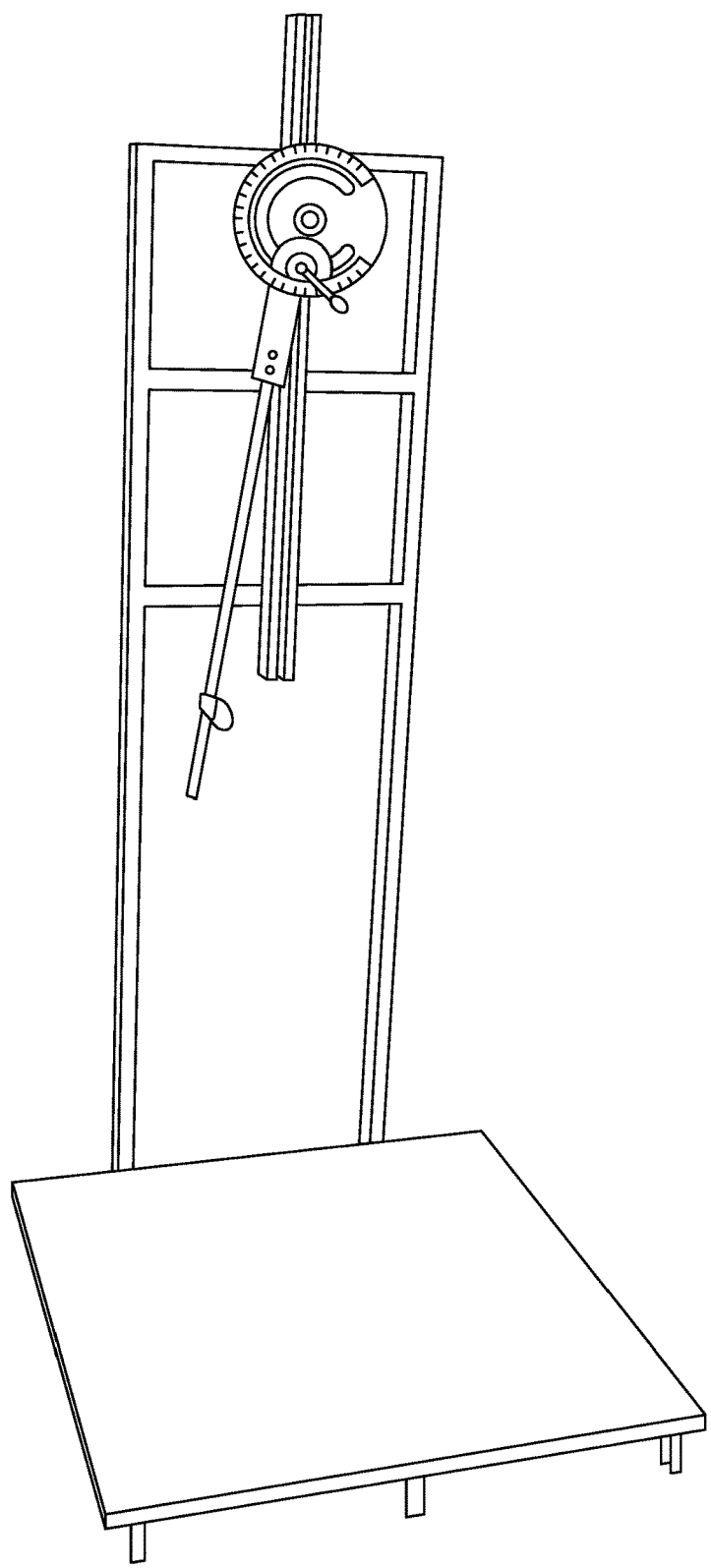
FIG. 14 shows the physical therapy device in a free standing platform arrangement.

FIG. 14 shows the physical therapy device in a free standing platform arrangement.

Figure 15:
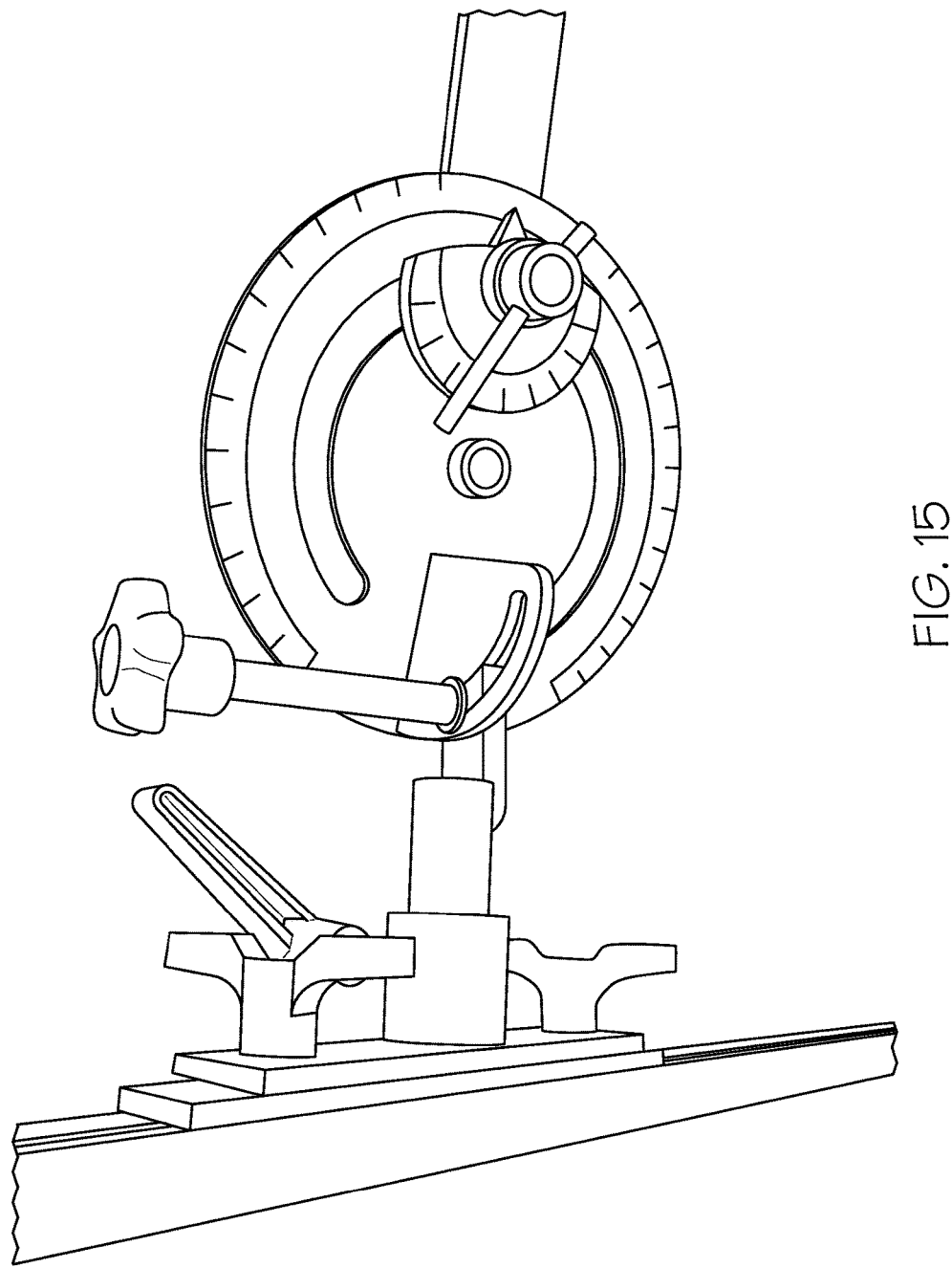
FIG. 15 shows two pivots, a horizontal/vertical pivot attached to the rail and a 90° pivot which allows the device to be rotated to be parallel to the wall (or door) or perpendicular to the wall (or door).

FIG. 15 shows two pivots, a horizontal/vertical pivot attached to the rail and a 90° pivot which allows the device to be rotated to be parallel to the wall (or door) or perpendicular to the wall (or door).

Figure 16:
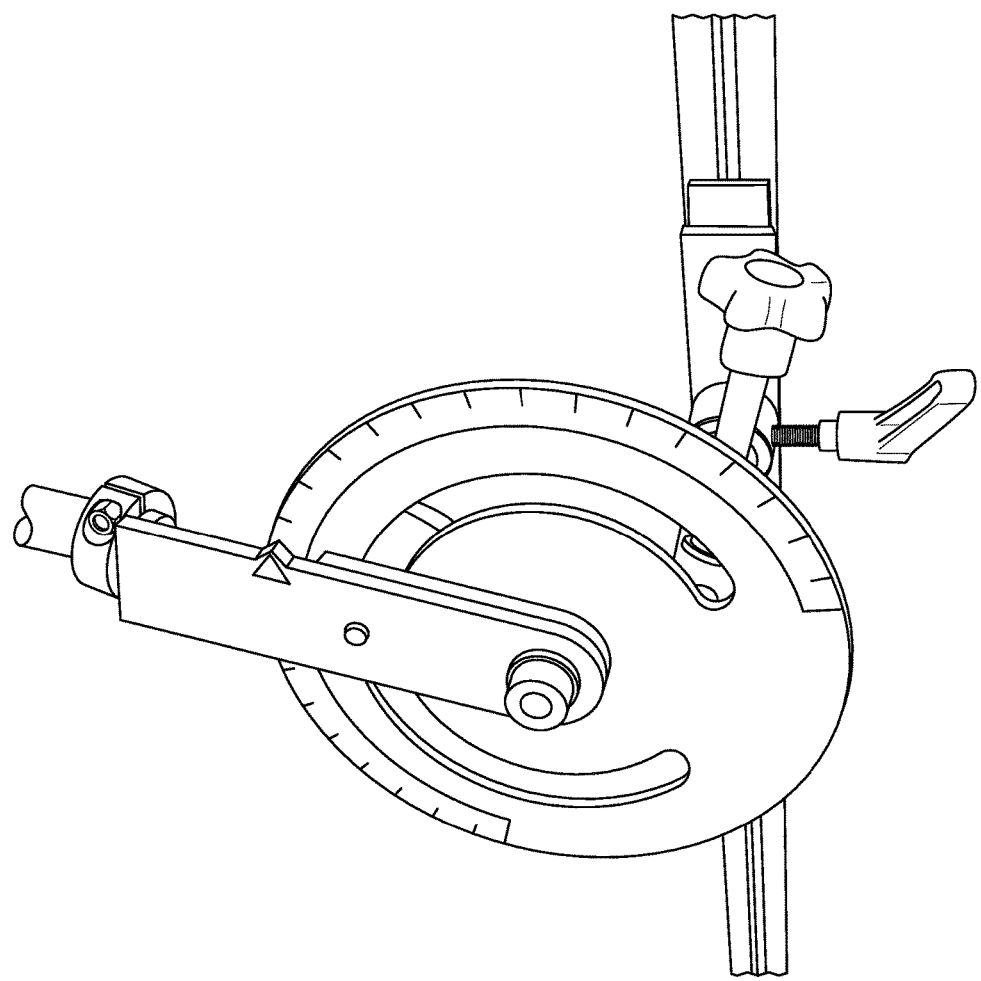
FIG. 16 shows the 90° pivot set to allow the device to move in the vertical plane parallel to the wall.

FIG. 16 shows the 90° pivot set to allow the device to move in the vertical plane parallel to the wall.

Figure 17:
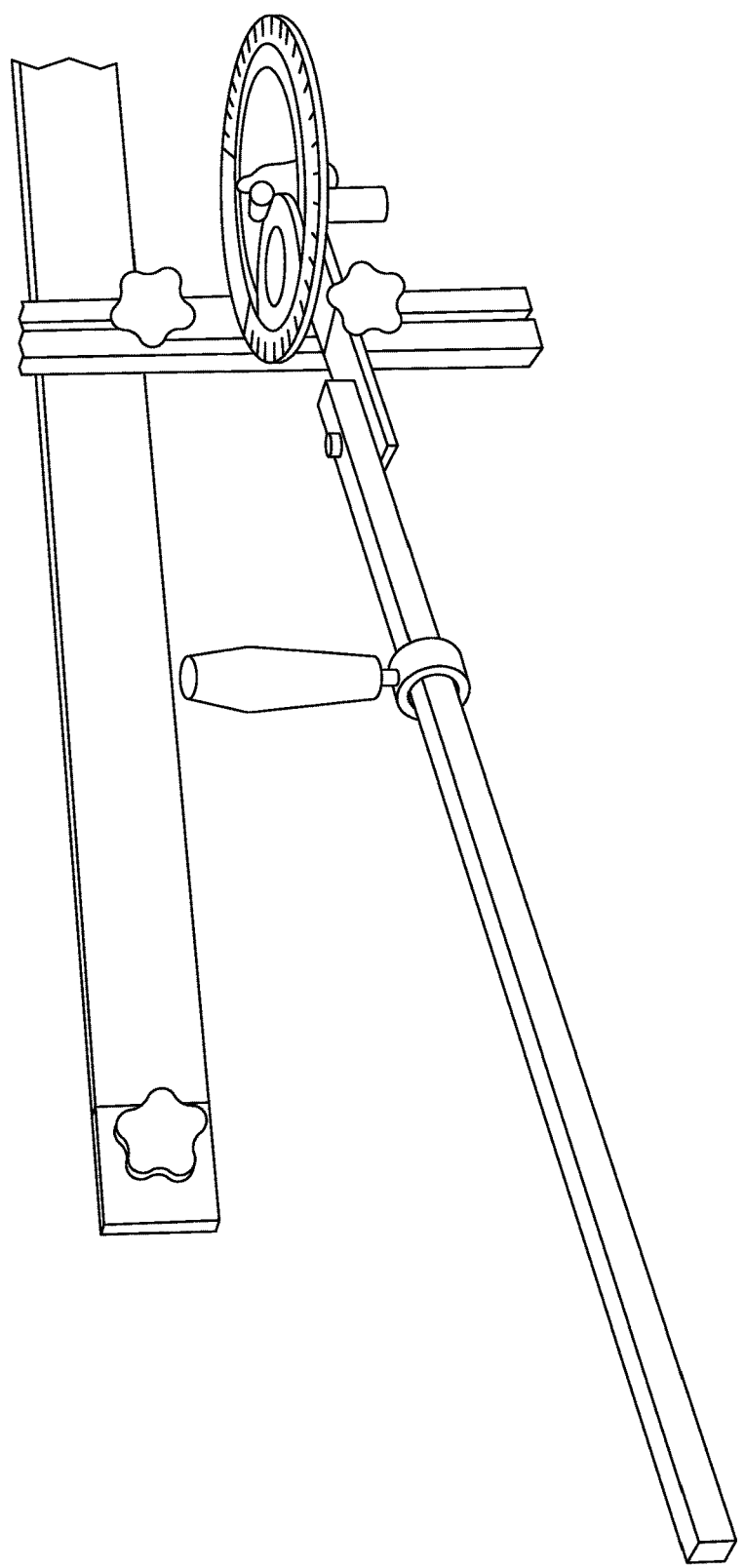
FIG. 17 shows the device pivoted to the horizontal position to allow movement in the horizontal plane.

FIG. 17 shows the device pivoted to the horizontal position to allow movement in the horizontal plane.

Figure 18:
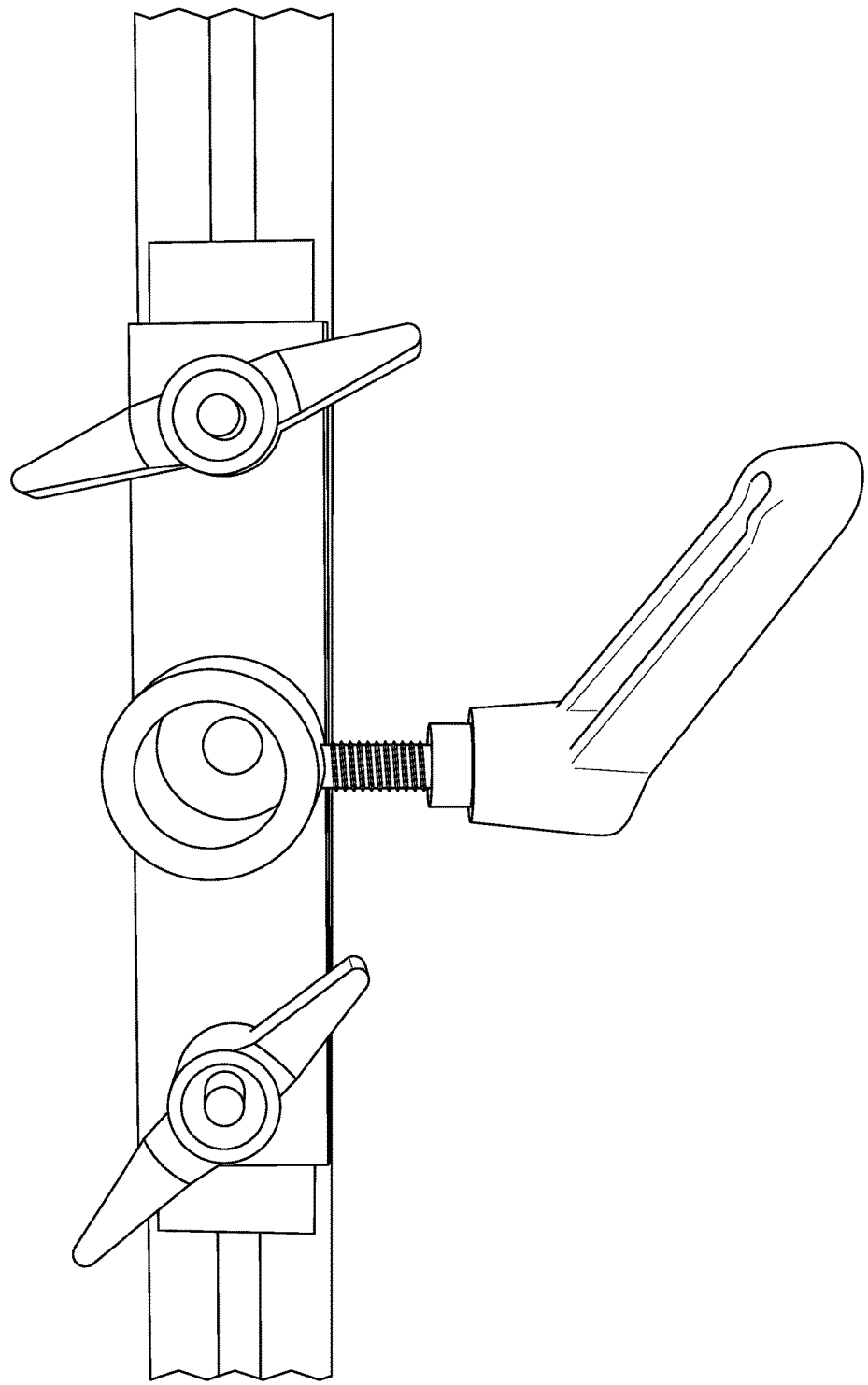
FIG. 18 shows the vertical/horizontal pivot in more detail.

FIG. 18 shows the vertical/horizontal pivot in more detail.

Figure 19:
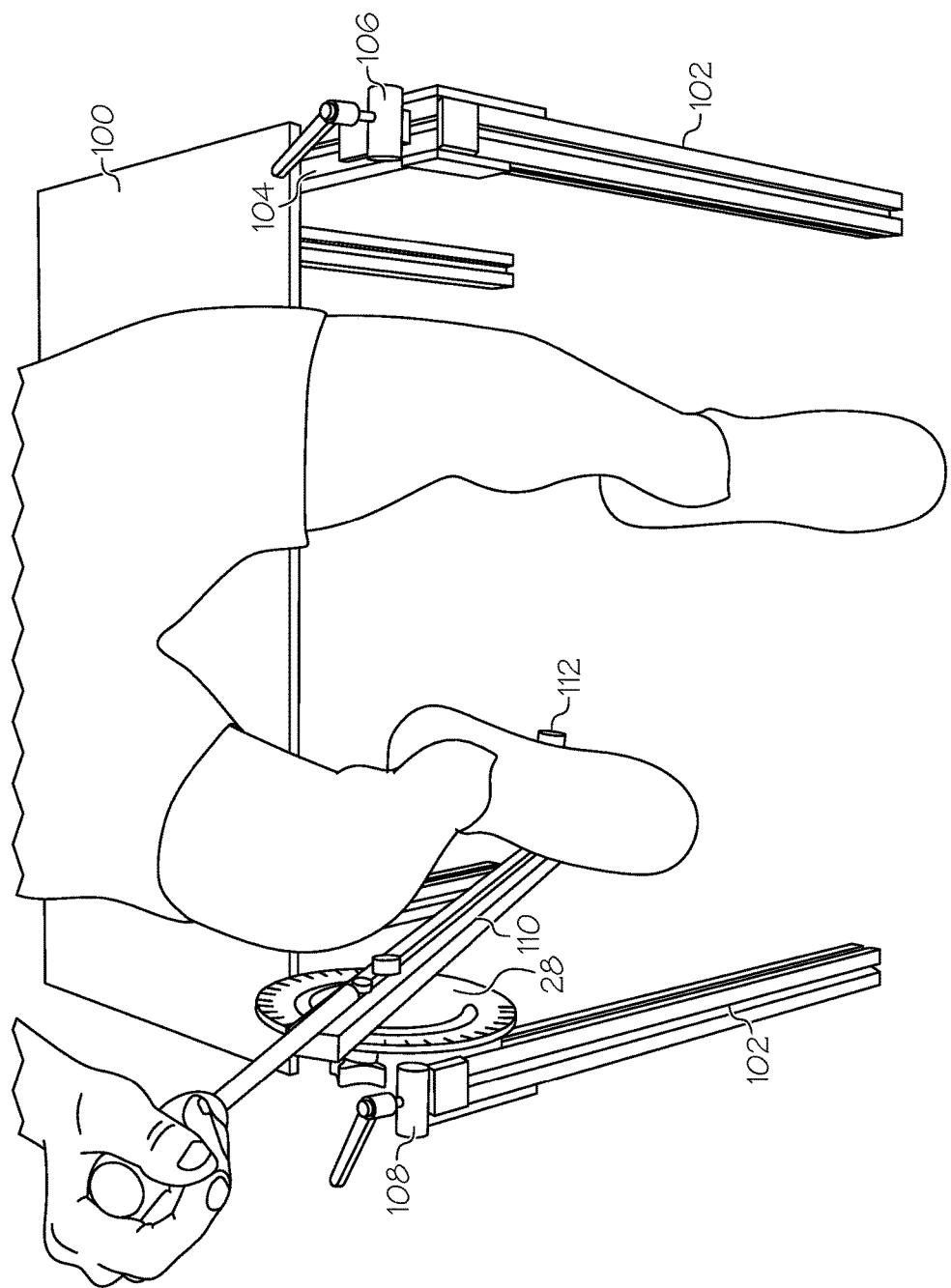
FIG. 19 shows a bench embodiment of the invention for the right knee.

FIG. 19 shows a bench embodiment of the invention in which the bench is shown at 100, supported by four legs 102. The bench has horizontal supports 104, one positioned to each side of the knee of a patient. A pair of quick attach devices 106 and 108 are positioned to the left knee and right knee of the patient. FIG. 19 shows the body 28 with leg 110 and footrest 112 connected to right leg quick connector 108. An L-bracket 114 (best shown in FIG. ??) is connected to body 28 and is frictionally engaged by quick connects 108 and 106.

Figure 20:
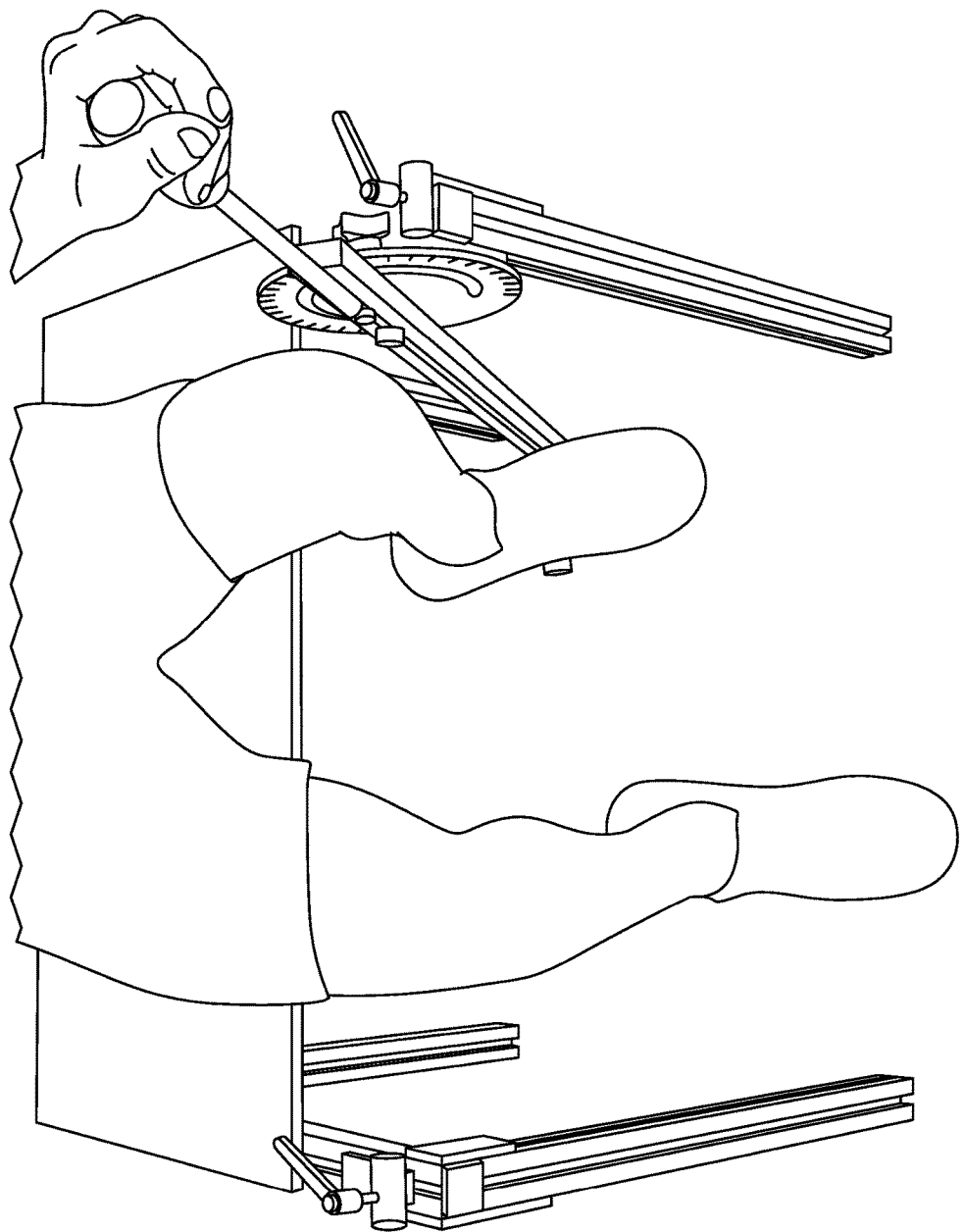
FIG. 20 shows a bench embodiment of the invention for the left knee.

FIG. 20 shows the bench embodiment with the body 28, leg 110 and footrest flipped around and connected to quick connect 106.

Figure 21:
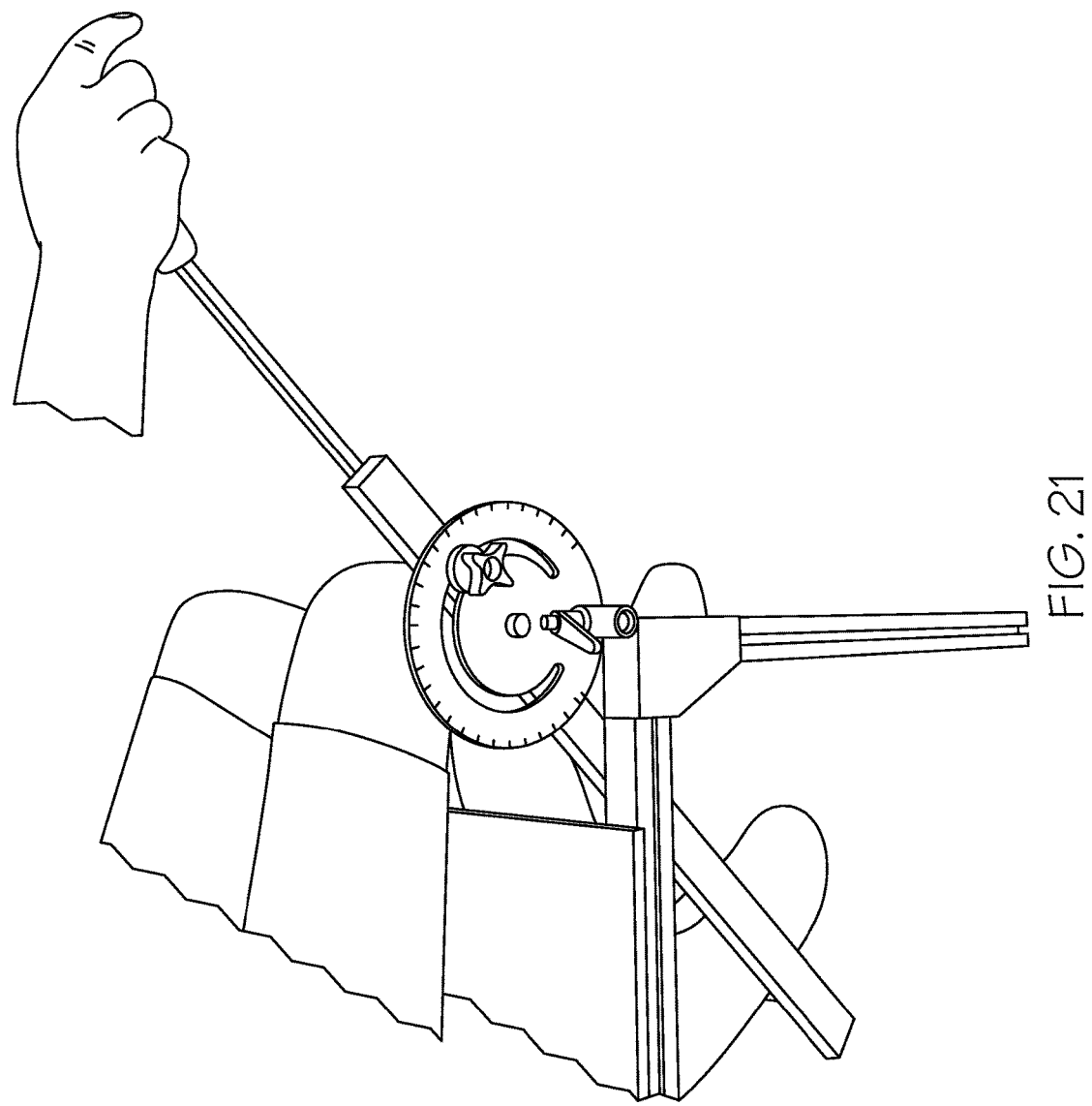
FIG. 21 shows the right knee in the back position.
Figure 22:
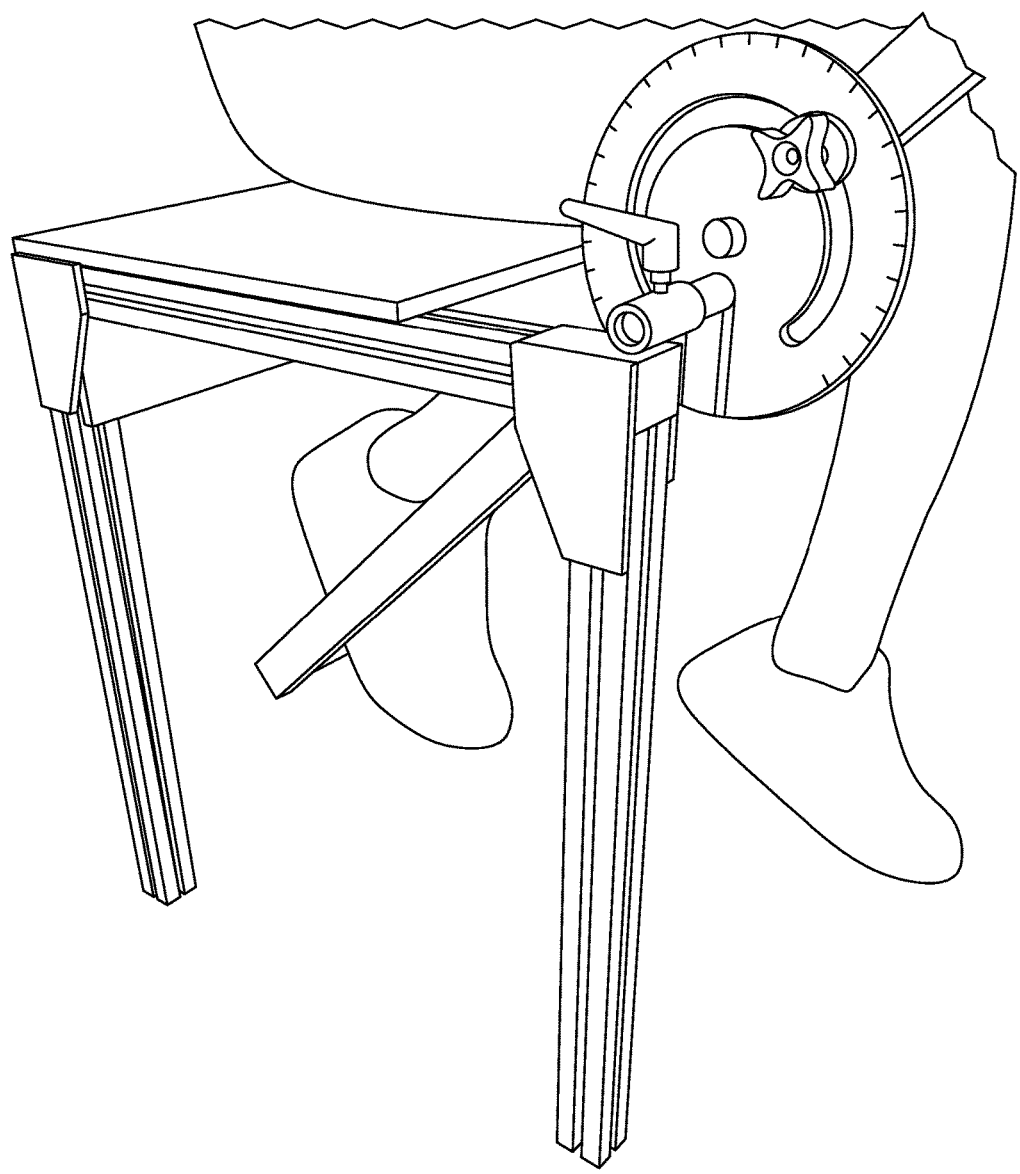
FIG. 22 shows the right knee in the back position from another angle.
Figure 23:
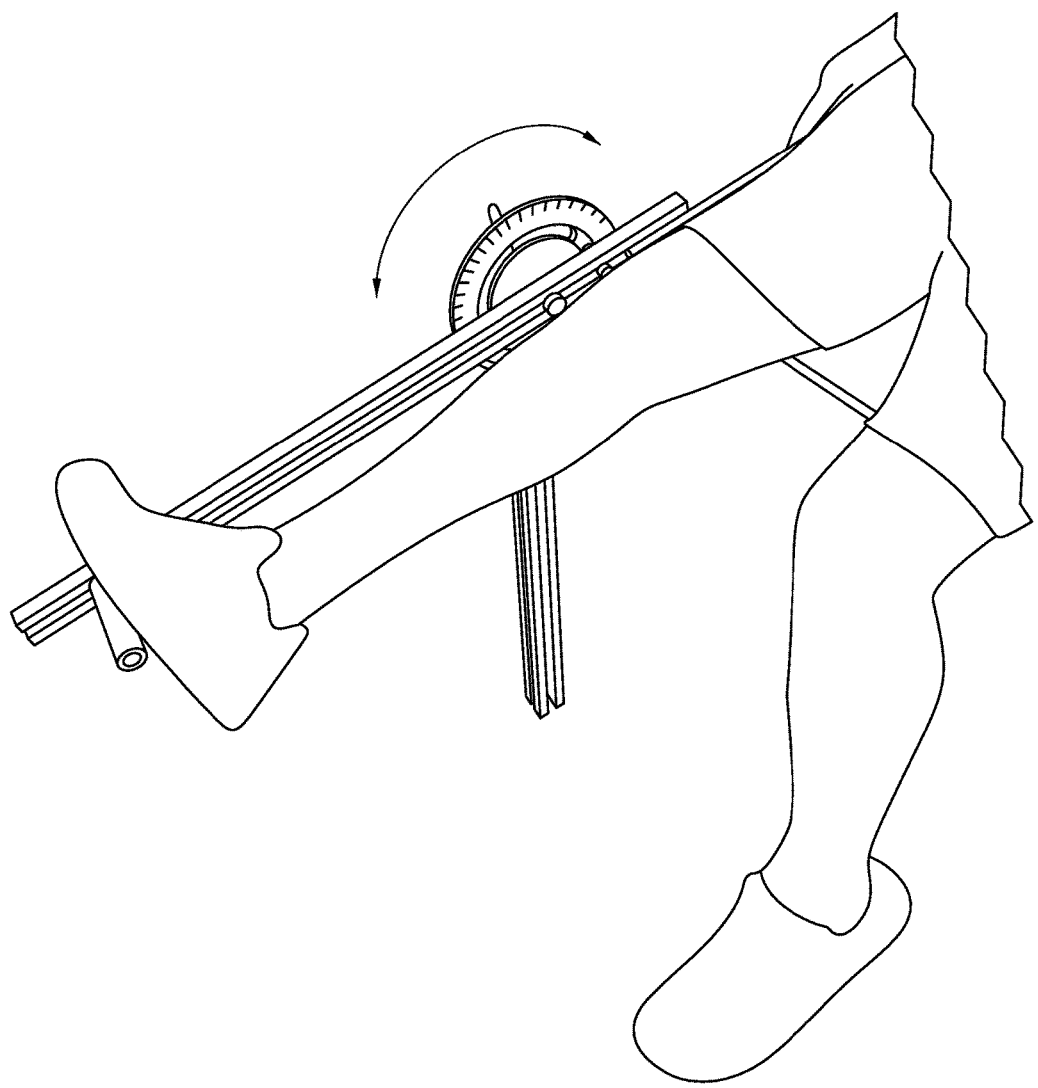
FIG. 23 shows the right knee in the forward position.
Figure 24:
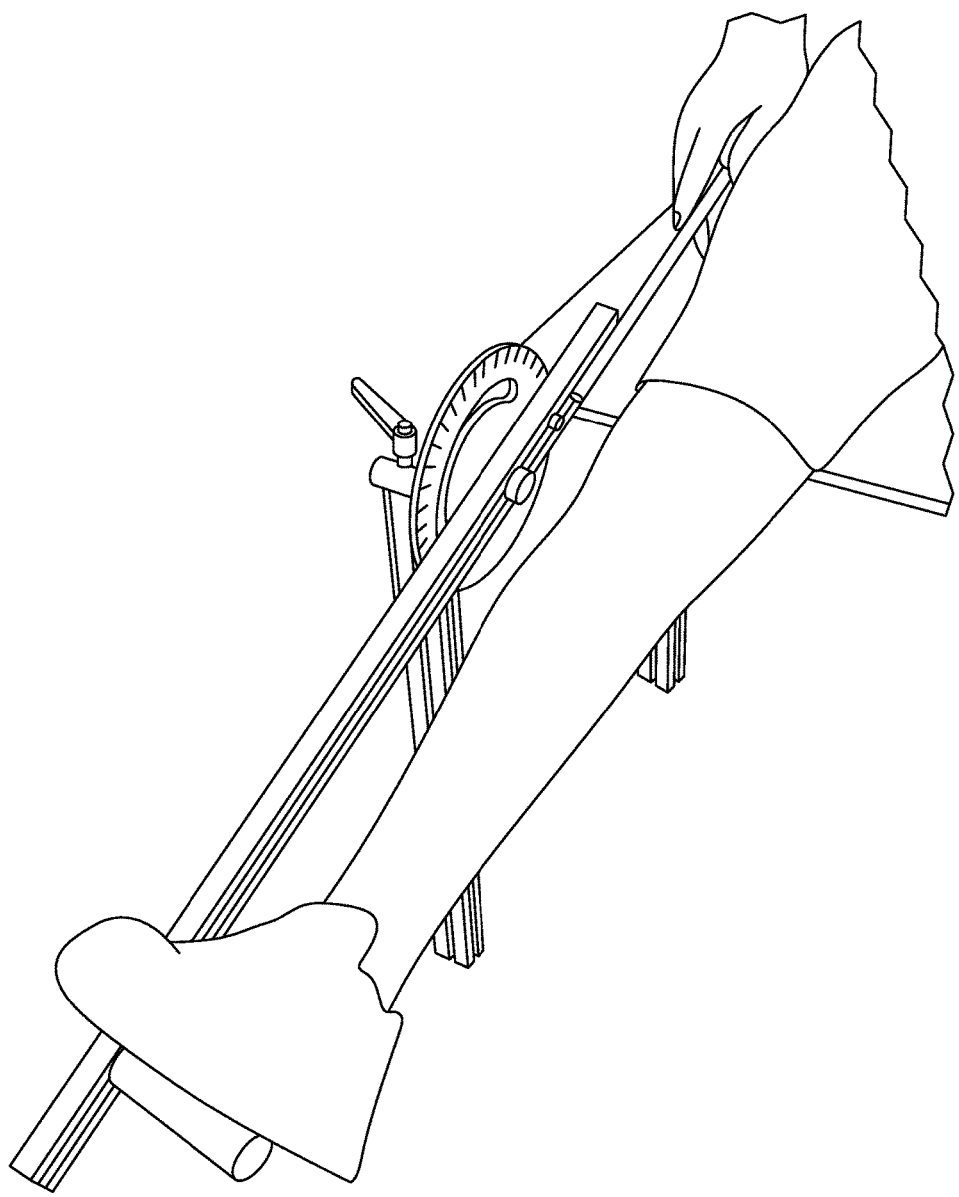
FIG. 24 shows the right knee in the forward position from another angle.

FIG. 21 and FIG. 22 show the leg in the rear position, while FIG. 23 and FIG. 24 show the leg in the extended front position. The adjustment mechanism 56 allows the force required to pivot leg 110 from the back position to the front position, to provide therapy to the knee.

Figure 25:
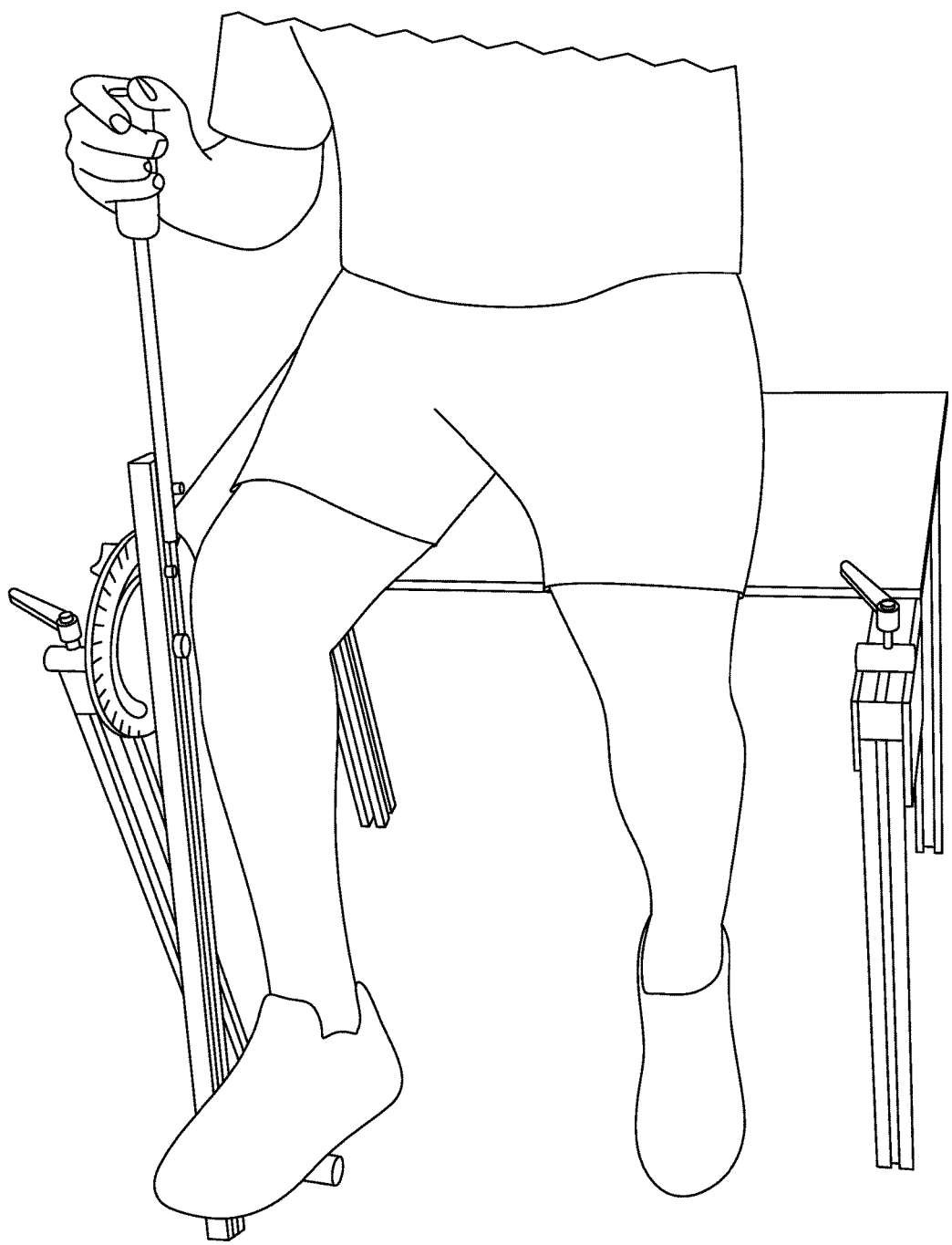
FIG. 25 shows the right knee in the neutral position.
Figure 26:
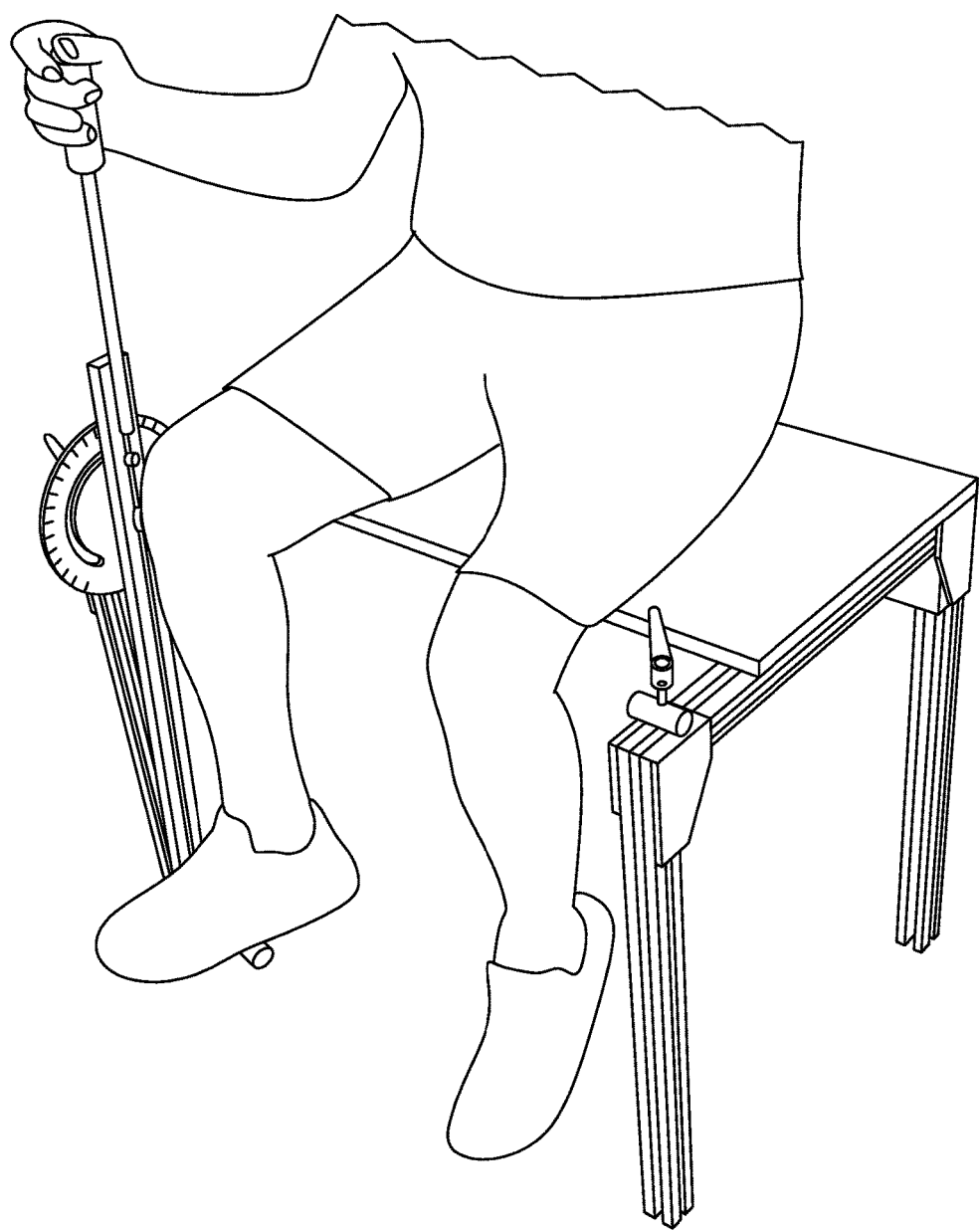
FIG. 26 shows the right knee in the neutral position from another angle.
Figure 27:
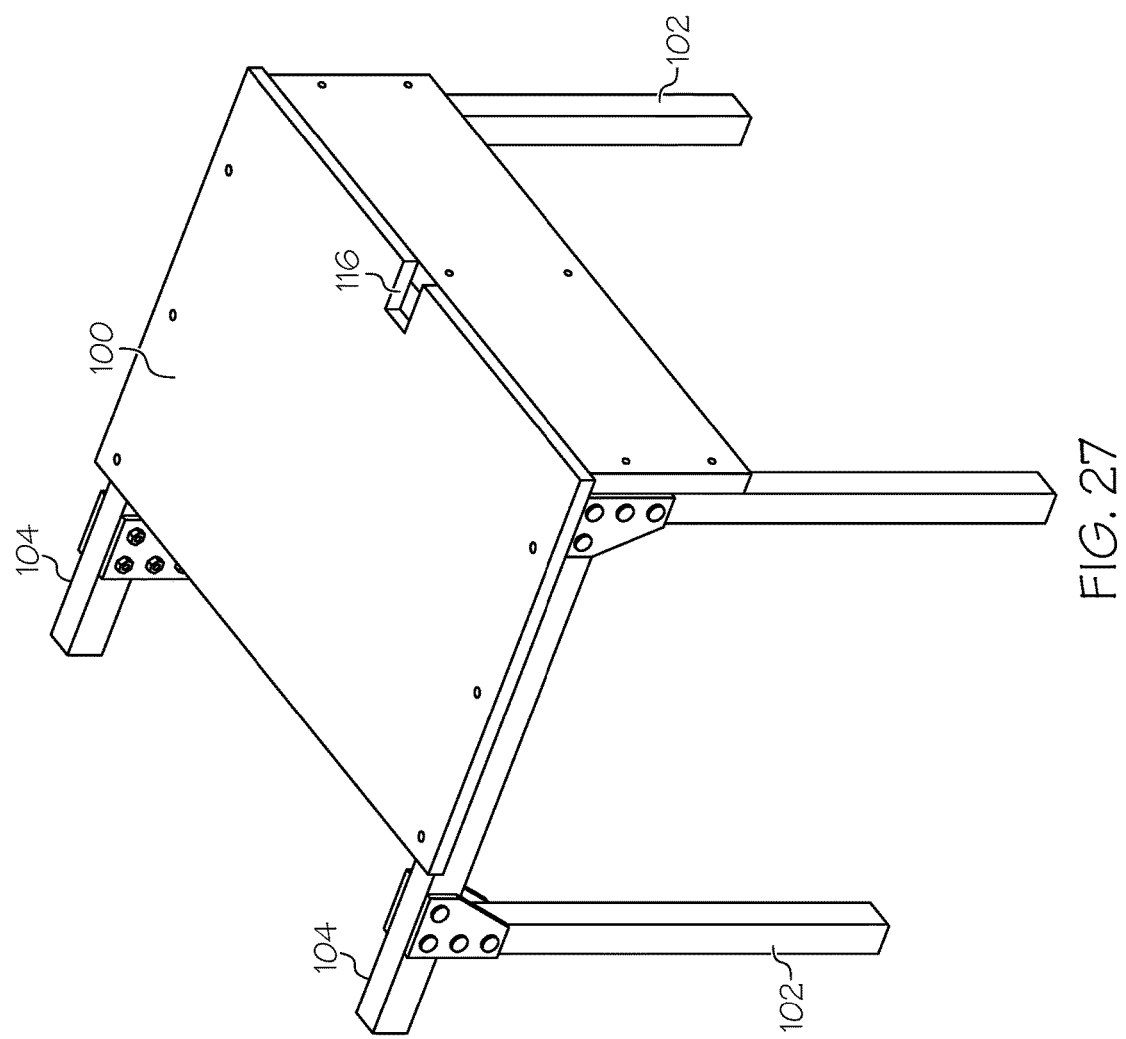
FIG. 27 shows the parts of the bench.

FIG. 25 shows the leg coming back to the neutral position of FIG. 26, with the leg bend 90 degrees at the knee.

Referring now to FIGS. 27 to 34, an embodiment of the bench version of the invention is shown with a slot 116 for attaching a shoulder rotator version of the invention, for a combination knee and shoulder version of the invention.

Figure 28:
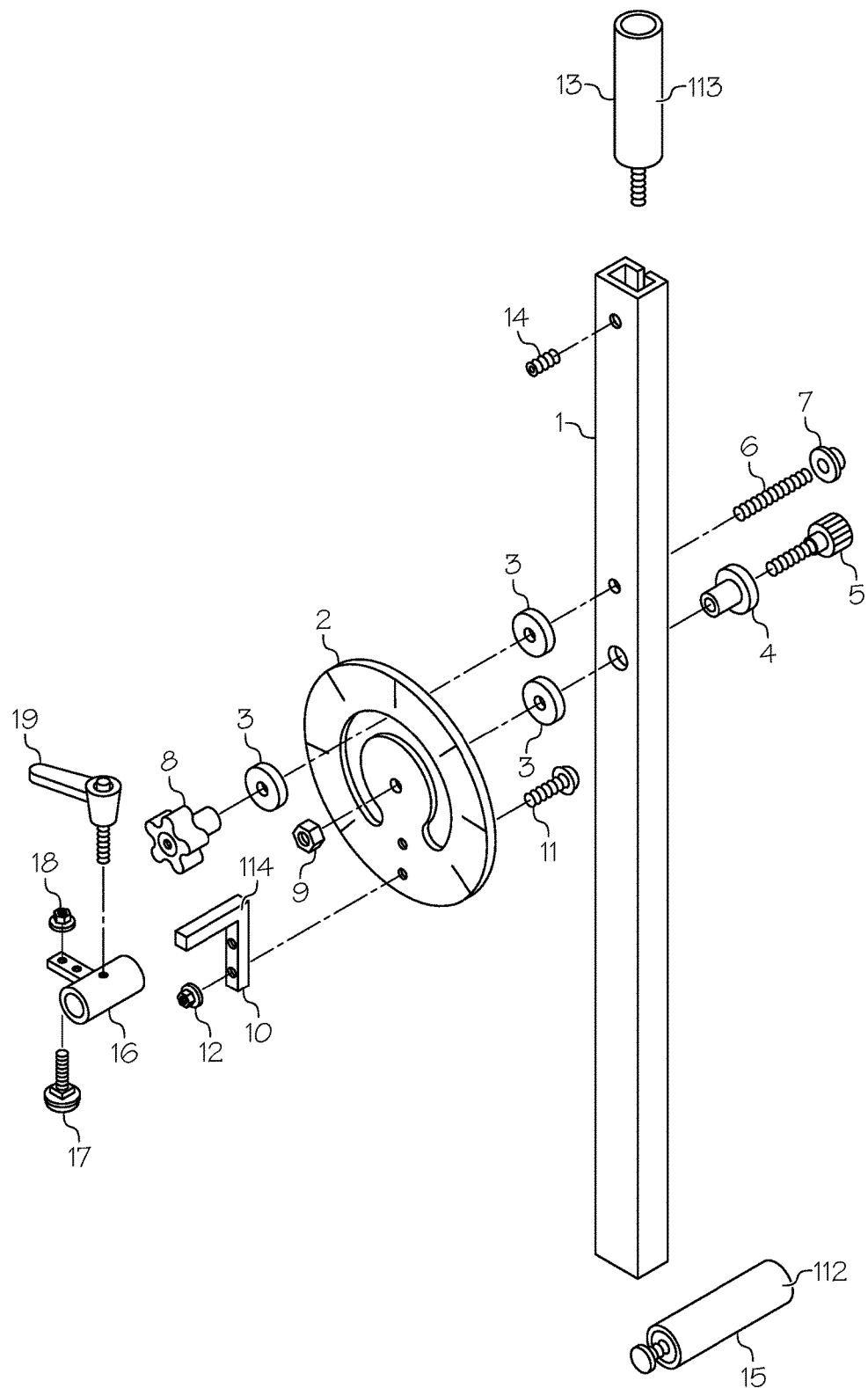
FIG. 28 shows the parts assembly for the knee embodiment.

FIG. 28 shows the parts of the knee rotator version of the invention, with the leg rail shown at 110, the footrest shown at 112, a hand grip shown at 113 and the bracket 114, which is used to connect the therapy device to quick connects 106 and 108.

Figure 29:
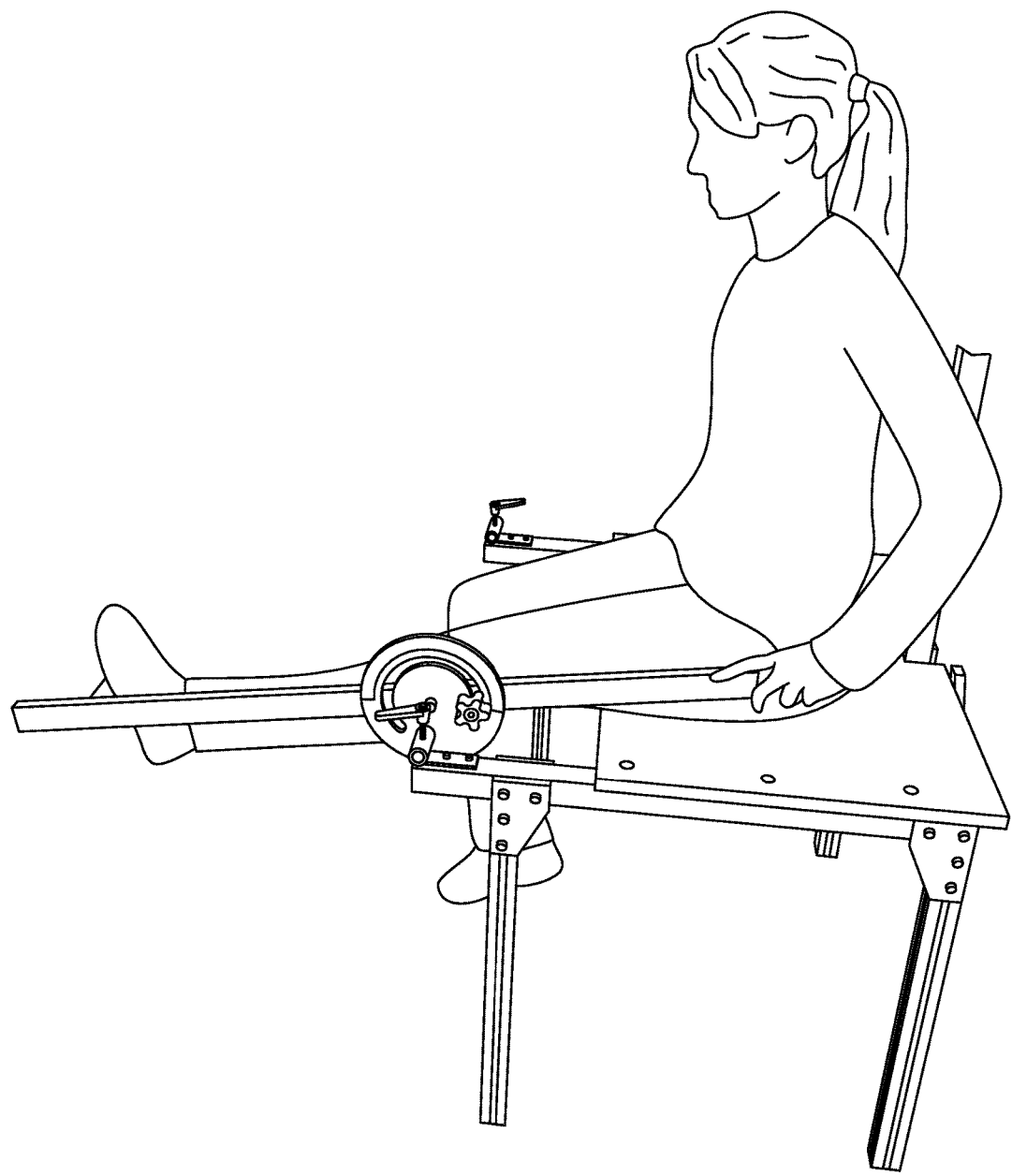
FIG. 29 shows the left knee in the forward position.
Figure 30:
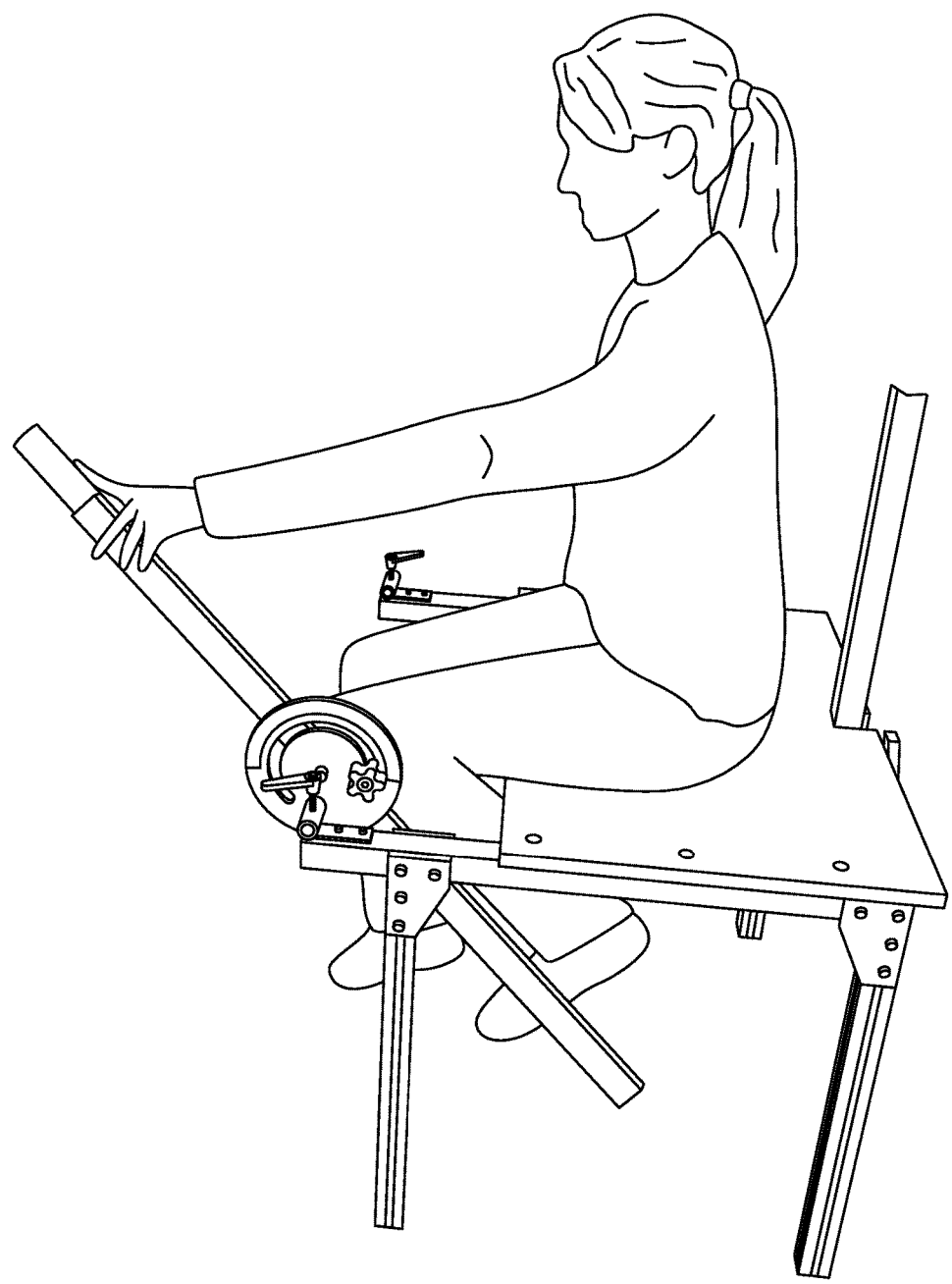
FIG. 30 shows the left knee in the back position.

FIGS. 29 and 30 show the left leg in the forward position and the rear position, with the adjustment mechanism 56 set to provide an adjustable amount of force to move the leg 110 between the two positions.

Figure 31:
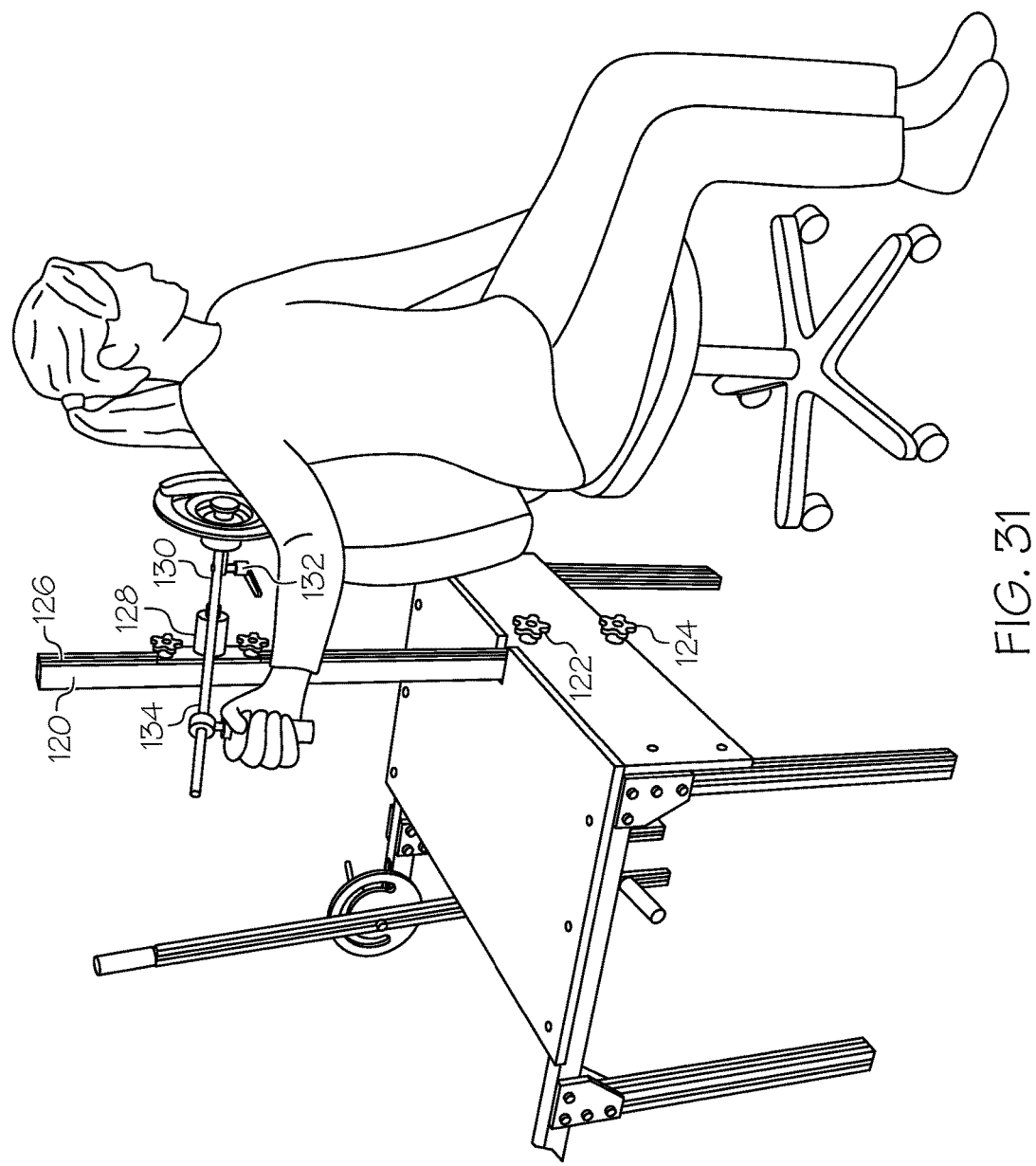
FIG. 31 shows the shoulder version of the bench, with the right arm in a neutral position.

FIG. 31 shows a shoulder frame 120 locked into slot 116 by connectors 122 and 124. Frame 120 has track 126 and height adjustment device 128 can lock the device in the track at the selected height. Arm 134 is connected to 128 via rod 130 using quick connect 132. A hand hold 136 is adjustable connected to arm 134.

Figure 32:
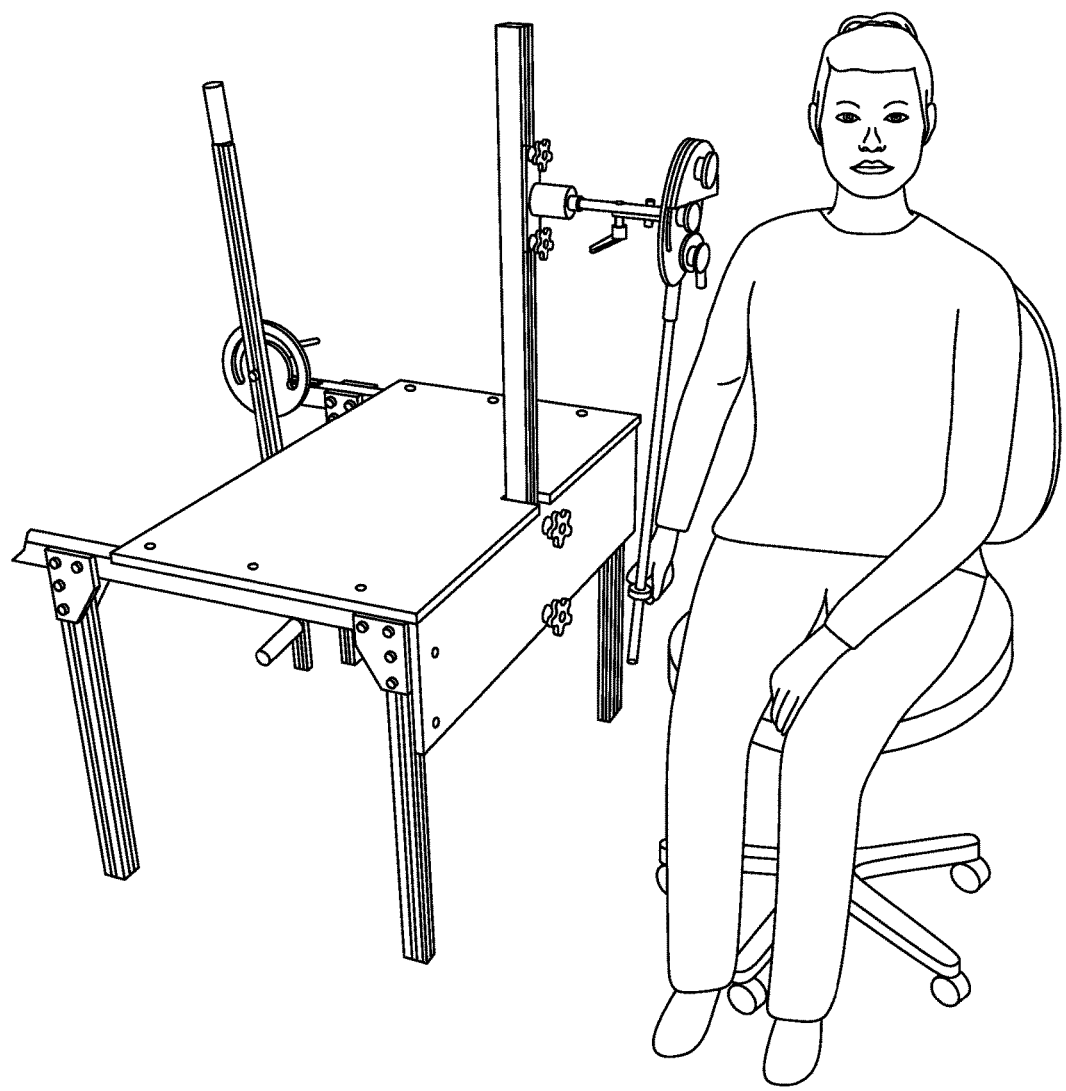
FIG. 32 shows the right shoulder in the down position.
Figure 33:
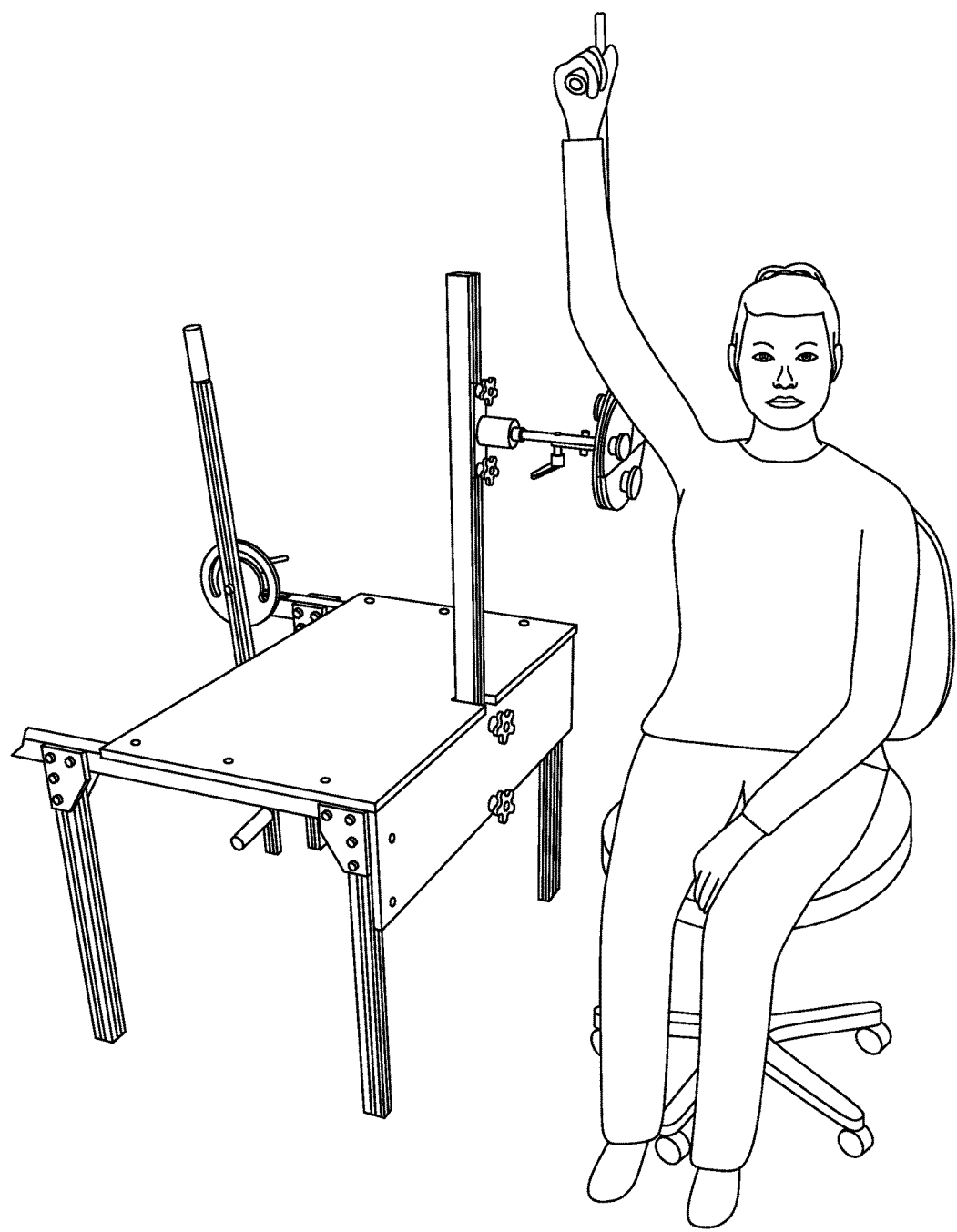
FIG. 33 shows the right shoulder in the up position.

FIG. 32 shows the device with the patients arm in the down position and FIG. 33 shows the device with the patients arm in the up position. The adjustment mechanism 56 allows the force required to move between the two positions to be adjusted, to provide therapy for the shoulder. By the patient reversing the chair 180 degrees, they can exercise the other arm.

Figure 34:
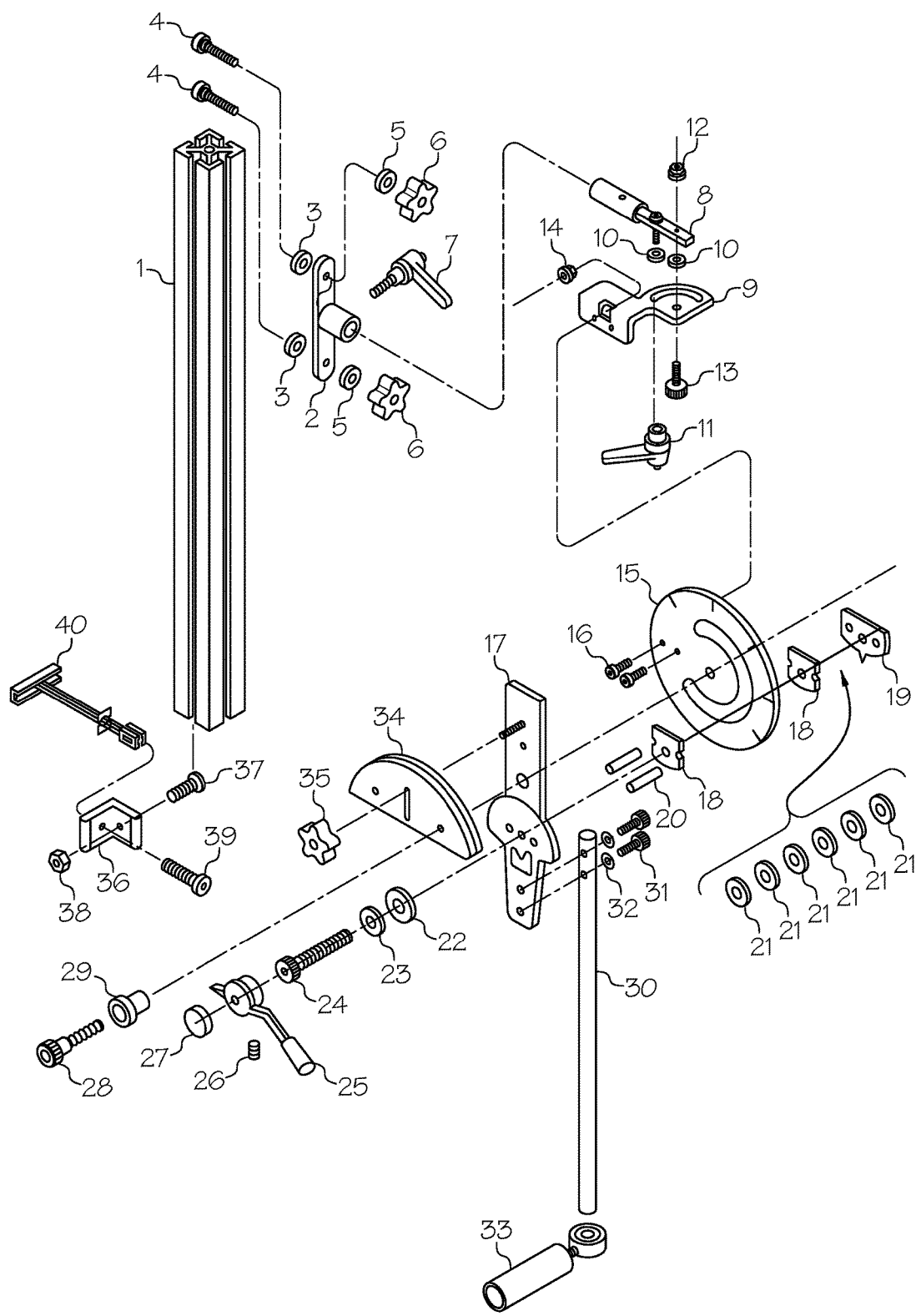
FIG. 34 shows the parts assembly for the shoulder embodiment.

FIG. 34 shows the parts of the shoulder rotator.

The above disclosure is intended to be illustrative and not exhaustive. This description will suggest many variations and alternatives to one of ordinary skill in this field of art. All these alternatives and variations are intended to be included within the scope of the claims where the term "comprising" means "including, but not limited to." Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

The invention claimed is:

1. A physical therapy device for a knee comprising:
   a bench having a seating surface and legs and a pair of horizontal supports positioned to either side of the knees of a person seated on the bench;
   a quick release securing device connected to each of the pair of supports;
   a rail connected to one of the quick release securing devices;
   a body pivotally attached to said rail;
   a foot rest attached to said rail and the foot rest and rail arranged to rotate with respect to said body about a pivot axis;
   the body having an adjustment mechanism to adjust the amount of force required to rotate the rail with respect to the body;

wherein said body is repositionable between first and second positions, to provide physical therapy to the knee.

2. The physical therapy device for a knee of claim 1 configured and arranged for the right knee.

3. The physical therapy device for a knee of claim 1 configured and arranged for the left knee.

4. A physical therapy device for a knee and a shoulder comprising:
   a bench having a seating surface and legs and a pair of horizontal supports position to either side of the knees of a person seated on the bench;
   a knee quick release securing device connected to each of the pair of supports;
   a rail connected to one of the knee quick release securing devices;
   a knee body pivotally attached to said rail;
   a foot rest attached to said rail and the foot rest and rail arranged to rotate with respect to said knee body about a pivot axis;
   the knee body having an adjustment mechanism to adjust the amount of force required to rotate the rail with respect to the knee body;
   a shoulder frame member connected to a shoulder frame member support, which is connected to the bench, the shoulder frame member having a vertical track;
   a shoulder quick release securing device arranged to slide in the vertical track and lockable into any positioned vertically along the vertical track;
   a shoulder body attachable to said shoulder quick release securing device;
   an arm attached to said shoulder body and arranged to rotate with respect to said body about a pivot axis;
   the shoulder body having an adjustment mechanism to adjust the amount of force required to rotate the arm with respect to the shoulder body, and
   a grip attached to said arm, said grip attachable to said arm in a plurality of positions.

\* \* \* \* \*

UNITED STATES PATENT AND TRADEMARK OFFICE
CERTIFICATE OF CORRECTION

| | |
|---|---|
| PATENT NO. | : 9,999,561 B2 |
| APPLICATION NO. | : 15/840423 |
| DATED | : June 19, 2018 |
| INVENTOR(S) | : Carol Nelson |

Page 1 of 1

It is certified that error appears in the above-identified patent and that said Letters Patent is hereby corrected as shown below:

In the Claims

Column 10, Line 8, delete "positioned" and replace with "position".

Signed and Sealed this
Seventh Day of August, 2018

Andrei Iancu
*Director of the United States Patent and Trademark Office*